(12) United States Patent
Pieper et al.

(10) Patent No.: US 8,557,773 B2
(45) Date of Patent: Oct. 15, 2013

(54) TREATMENT OF BLEEDING WITH LOW HALF-LIFE FIBRINOGEN

(75) Inventors: Frank Pieper, Heemstede (NL);
Anurag Relan, Los Angeles, CA (US);
Erik Jordahl Forsberg, Fitchburg, WI (US)

(73) Assignee: Laboratoire Francais du Fractionnement et des Biotechnologies, Les Ulis (FR)

( * ) Notice: Subject to any disclaimer, the term of this patent is extended or adjusted under 35 U.S.C. 154(b) by 121 days.

(21) Appl. No.: 12/990,643

(22) PCT Filed: Apr. 29, 2009

(86) PCT No.: PCT/NL2009/050234
§ 371 (c)(1),
(2), (4) Date: Feb. 21, 2011

(87) PCT Pub. No.: WO2009/134130
PCT Pub. Date: Nov. 5, 2009

(65) Prior Publication Data
US 2011/0263503 A1    Oct. 27, 2011

Related U.S. Application Data

(60) Provisional application No. 61/050,174, filed on May 2, 2008.

(51) Int. Cl.
*A61K 38/36*    (2006.01)
*C07K 14/75*    (2006.01)

(52) U.S. Cl.
USPC .......................... 514/13.6; 435/69.6; 530/382

(58) Field of Classification Search
None
See application file for complete search history.

(56) References Cited

U.S. PATENT DOCUMENTS 6,780,411 B2 *    8/2004    Lewis et al. ................. 424/94.64
6,825,323 B2 *    11/2004    Hess .............................. 530/384
6,984,772 B1    1/2006    Velander

FOREIGN PATENT DOCUMENTS

WO    WO 9607728 A1 *    3/1996

OTHER PUBLICATIONS

Bocci, "The role of sialic acid in determining the life-span of circulating cells and glycoproteins," Experientia, vol. 32, No. 2; pp. 135-140 (1976).
Coller, "Asialofibrinogen supports platelet aggregation and adhesion to glass," Blood, vol. 53, No. 2; pp. 325-332 (1979).
Diaz-Maurino et al., "Desialylation of fibrinogen with neuraminidase. Kinetic and clotting studies," Thrombosis Research, vol. 27, No. 4; pp. 397-403 (1982).
Hager et al., "Age dependency of the sialic acid content of fibrinogen. Consequences for erythrocyte aggregation," Archives of Gerontology and Geriatrics, Elsevier Science Publishers B.V., vol. 12, No. 1; pp. 25-30 (1991).
Maghzal et al., "The sialic acid content of fibrinogen decreases during pregnancy and increases in response to fibrate therapy," Thrombosis Research, vol. 115, No. 4; pp. 293-299 (2005).

(Continued)

*Primary Examiner* — Jeffrey E Russel
(74) *Attorney, Agent, or Firm* — Foley & Lardner LLP

(57) ABSTRACT

The invention provides low-half life fibrinogen with reduced sialyation as a result of recombinant expression or enzymatic and chemical removal. The low-half life fibrinogen is useful in treating or effecting prophylaxis of bleeding particularly in situations of an acute nature in which a high initial dose and rapid decline to normal or below normal levels is desirable.

14 Claims, 10 Drawing Sheets

(56) References Cited

OTHER PUBLICATIONS

Martinez et al., "Functional and metabolic properties of human asialofibrinogen," Journal of Laboratory and Clinical Medicine, Mosby, Inc., US, vol. 89, No. 2; pp. 367-377 (1977).

PCT Search Report of Oct. 23, 2009 for application PCT/NL2009/050234.

Regoeczi et al., "Effects of intravenous neuraminidase on the turnover of fibrinogen," CIBA Foundation Symposium 1972, vol. 9, pp. 181-201 (1972).

Roy et al., "Secretion of biologically active recombinant fibrinogen by yeast," Journal of Biological Chemistry, The American Society for Biochemistry and Molecular Biology, Inc., vol. 270, No. 40; pp. 23761-23767 (1995).

Solis et al., "Does fibrinogen contain populations with different degree of sialylation?," Thrombosis Research, vol. 67, No. 6; pp. 631-641 (1992).

Tojo et al., "Recombinant human fibrinogen expressed in the yeast *Pichia pastoris* was assembled and biologically active," Protein Expression & Purification, vol. 59, No. 2; pp. 289-296 (2008).

* cited by examiner

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Synthesized

<400> SEQUENCE: 1

Gly Pro Arg Pro
 1

TREATMENT OF BLEEDING WITH LOW HALF-LIFE FIBRINOGEN

BACKGROUND OF THE INVENTION

Fibrinogen, the main structural protein in the blood responsible for the formation of clots, exists as a dimer of three polypeptide chains; the Aα (66.5 kD), Bβ (52 kD) and γ (46.5 kD) are linked through 29 disulphide bonds. The addition of asparagine-linked carbohydrates to the Bβ and γ chains results in a molecule with a molecular weight of 340 kD. Fibrinogen has a trinodal structure, a central nodule, termed the E domain, contains the amino-termini of all 6 chains including the fibrinopeptides (Fp) whereas the two distal nodules termed D domains contain the carboxy-termini of the Aα, Bβ and γ chains. Fibrinogen is proteolytically cleaved at the amino terminus of the Aα and Bβ chains releasing fibrinopeptides A and B (FpA & FpB) and converted to fibrin monomer by thrombin, a serine protease that is converted from its inactive form by Factor Xa. The resultant fibrin monomers non-covalently assemble into protofibrils by DE contacts on neighboring fibrin molecules.

REFERENCE TO A "SEQUENCE LISTING", A TABLE, OR A COMPUTER PROGRAM LISTING

The Sequence Listing written in file 397876SEQLIST.txt is 558 bytes and was created on Feb. 20, 2013. The information contained in this file is hereby incorporated by reference.

Fibrinogen is naturally subject to phosphorylation, sulfation, and glycosylation. Glycosylation is a complex process of post-translational modification and has important functions in secretion, protein folding, immunogenicity and clearance of glycoproteins from the bloodstream. Glycoprotein glycans are mainly attached to proteins via an N- or an O-glycosidic bond. N-linked glycosylation occurs to the side-chain group of an Asparagine (Asn) residue, whereas O-linked glycosylation occurs to the side-chain group of Ser or Thr. It is well established that human fibrinogen contains glycans linked to Asn residues in the Bβ and gamma chains in the Asn-Arg-Thr (Asn at position 364) and Asn-Lys-Thr (Asn at position 52) sequence, respectively (Topfer-Peterson, 1976, *Hoppe Seylers Z Physiol Chem* 357:1509; Blomback, 1973, *J. Biol. Chem* 248:5806).

The current standard of care for patients with fibrinogen deficiencies involves replacement therapy with human fibrinogen containing preparations such as plasma-derived fibrinogen (pdFIB), or fresh-frozen plasma and cryoprecipitates, both of which contain pdFIB.

Although therapy with human fibrinogen containing preparations can be effective at controlling bleeding, pathologic thromboses with serious sequalae are well-known complications of such infusions (Lak, Br J Haematol, 1999 October; 107(1):204-6). Often the abnormal clots can occur after the initial bleeding episode has been treated (Pati, Surg. Neurol. 2008 Feb. 22; Matsumoto, Haemophilia 2008 January; 14(1):153-6). In the broader setting of hereditary bleeding disorders, in which this phenomenon has also been observed, excessive levels of replaced clotting factors for prolonged durations have been thought to contribute to these events (Franchini, Thromb. Haemost. 2004 May; 91(5):1053-5). In the case of bleeding due to a deficiency of fibrinogen, replacement therapy with pdFIB has been directly implicated as a contributing factor in the etiology of pathologic thromboses (Kreuz, Transfus. Apher. Sci. 2005 June; 32(3):247-53).

SUMMARY OF THE INVENTION

The invention relates to a pharmaceutical composition comprising human fibrinogen having reduced half-life relative to natural plasma fibrinogen, and a pharmaceutically acceptable carrier. Preferably said fibrinogen has a sialic acid content of 0-2 moles sialic acid per mole fibrinogen. The invention also relates to the use of fibrinogen having a reduced half-life relative to natural human plasma fibrinogen in the manufacture of a medicament for the treatment or prophylaxis of bleeding in a patient who is bleeding or is at risk of bleeding. Preferably said fibrinogen is under-sialyated and recombinant or derived from plasma. Furthermore, the invention relates to the use of fibrinogen having a reduced half-life relative to natural human plasma fibrinogen in the manufacture of a medicament for the treatment or prophylaxis of bleeding in a patient who is bleeding or is at risk of bleeding, wherein the treatment is in a regime sufficient to achieve a peak concentration of fibrinogen in plasma including administered and endogenous fibrinogen that is within or above normal levels, and wherein the plasma concentration declines to normal or below normal levels within three days of first administration.

The invention provides methods of treating or effecting prophylaxis in a patient who is bleeding or is at risk of bleeding, comprising administering a dose of fibrinogen having a reduced half-life relative to natural human plasma fibrinogen to the patient. In some methods, the fibrinogen is under-sialyated fibrinogen. In some methods, the fibrinogen is recombinant human fibrinogen. In some methods, the fibrinogen is human fibrinogen from plasma. In some methods, the half-life is reduced by a factor of at least 50% relative to that of human plasma fibrinogen. In some methods, the half-life is less than one day. In some methods, the dose is greater than 1 g. In some methods, the dose is greater than 3 g. In some methods, the dose is greater than 6 g. In some methods, the dose is greater than 10 g. In some methods, the dose is greater than 12 g. In some methods, the dose delivers a peak plasma concentration of recombinant and endogenous fibrinogen greater than 2 g/L. In some methods, the peak plasma concentration of recombinant and endogenous fibrinogen is greater than 6 g/L. In some methods, the peak plasma concentration of recombinant and endogenous fibrinogen is greater than 12 g/L. In some methods, the peak plasma concentration of recombinant fibrinogen is greater than 1 g/L. In some methods, the peak plasma concentration of recombinant fibrinogen is greater than 3 g/L. In some methods, the peak plasma concentration of recombinant fibrinogen is greater than 9 g/L. In some methods, the peak plasma concentration of recombinant fibrinogen is greater than 12 g/L. In some methods, a single dose is administered. In some methods, multiple doses are administered. In some methods, the fibrinogen is administered as a single dose or multiple doses all within a period of 24 hours per bleeding episode. In some methods, the bleeding results from an acute disorder. In some methods, the bleeding results from a traumatic injury. In some methods, the bleeding results from surgery. In some methods, the bleeding results from an inherited disorder.

The invention further provides a pharmaceutical composition comprising human fibrinogen having reduced half-life relative to natural plasma fibrinogen. Optionally, the human fibrinogen has a sialic acid content of 0-2 moles sialic acid per mole fibrinogen. The invention further provides methods of treating or effecting prophylaxis in a patient who is bleeding or at risk of bleeding, comprising administering fibrinogen having reduced half-life relative to natural human fibrinogen to the patient in a regime sufficient to achieve a peak concentration of fibrinogen in plasma including administered and endogenous fibrinogen that is within or above normal levels. In some methods, the plasma concentration of fibrinogen including administered and endogenous fibrinogen declines to normal or below normal levels within 3 days of first administration. In some methods, the plasma concentration of fibrinogen including administered and endogenous fibrinogen declines to normal or below normal levels within 2 days of first administration. In some methods, the plasma concentration of fibrinogen including administered and endogenous fibrinogen declines to normal or below normal levels within 1 day of first administration. In some methods, the peak plasma concentration of fibrinogen including administered and endogenous fibrinogen is above 2 g/L. In some methods, the peak plasma concentration of fibrinogen including administered and endogenous fibrinogen is above 6 g/L. In some methods, the peak plasma concentration of fibrinogen including administered and endogenous fibrinogen is above 10 g/L. In some methods, the peak plasma concentration of fibrinogen including administered and endogenous fibrinogen is above 12 g/L. In some methods, the peak plasma concentration of fibrinogen including administered and endogenous fibrinogen is 2-12 g/L. In some methods, the peak plasma concentration of fibrinogen including administered and endogenous fibrinogen is within 2-4 g/L and the plasma concentration of fibrinogen declines below 2 g/L within 1 day. In some methods, the bleeding results from trauma. In some methods, the bleeding results from surgery. In some methods, the bleeding results from an inherited disorder. In some methods, the bleeding results from an inherited or acquired deficiency in a coagulation protein. In some methods, the bleeding is a result of organ failure. In some methods, the bleeding is a result of an iatrogenic disorder. In some methods, the fibrinogen is administered once or at multiple times occurring within a period of no more than two hours. In some methods, the fibrinogen is administered multiple times at intervals no greater than two days.

The invention further provides methods of treating or effecting prophylaxis in a patient who is bleeding or at risk of bleeding, comprising selecting a regime of human fibrinogen based on a reduced half-life of the fibrinogen relative to the half life of natural human fibrinogen from plasma; and administering the regime to the patient. In some methods, a regime of recombinant human fibrinogen is selected. In some methods, the regime comprises administering a dose of human fibrinogen greater than 4 g to the patient. In some methods, the regime comprises administering the human fibrinogen at intervals of 24 hours or less. In some methods, the regime comprises administering a single dose of the human fibrinogen. In some methods, the regime comprises administering multiple doses of the human fibrinogen.

The invention further provides the use of recombinant fibrinogen at higher dose than plasma fibrinogen for an improved efficacy side effects profile.

The invention further provides the use of a reduced half-life of recombinant fibrinogen relative to plasma fibrinogen in determining a regime to administer the recombinant fibrinogen.

The invention further provides the use of recombinant fibrinogen to confer a peak concentration of fibrinogen in a patient that is at or above normal levels, wherein the concentration declines to normal or below normal levels within 12 hours.

Non-reduced rh-Fbg and h-Fbg respectively. Lane 3 and 4 reduced rh-Fbg and H-Fbg respectively. Molecular weight markers are indicated at the left.

Figure 11:
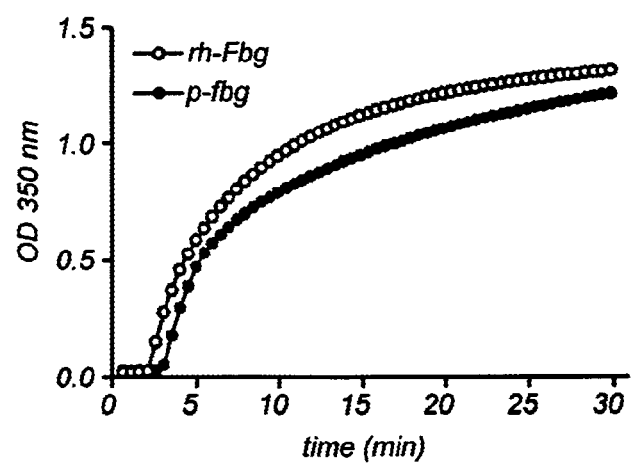

FIG. 11: Polymerization of GPRP-isolated recombinant and plasma-fibrinogen. Polymerization was initiated by the addition of thrombin (0.025 U/ml) in the presence of 1 mM EDTA to both fibrinogen preparations (0.5 mg/ml) and polymer formation was followed as change in turbidity at 350 nm in time. Similar results were obtained when polymerization was performed in the presence of 10 mM $Ca^{2+}$.

Figure 12:
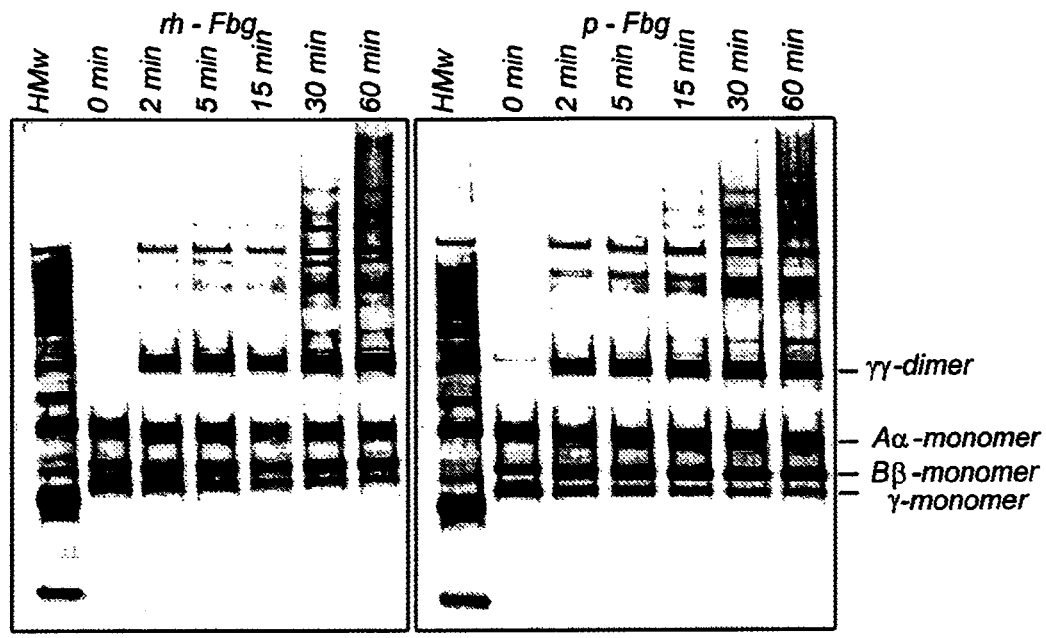

FIG. 12: Factor XIIIa-catalyzed cross-linking of recombinant fibrinogen (rh-Fbg) and plasma fibrinogen (h-Fbg) isolated according to the GPRP-method. At time 0, thrombin (1 U/ml) was added to a mixture of fibrinogen (60 µg/ml) and FXIII (1 U/ml) in the presence of $Ca^{2+}$ (25 mM/ml) for 5 min Samples were dissolved and run under reducing conditions on a 8% SDS-PAGE.

Figure 13:
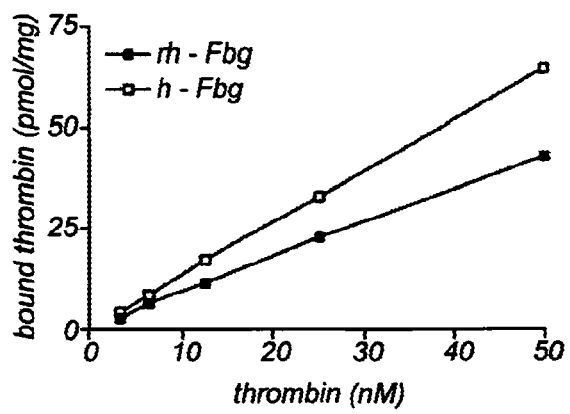

FIG. 13: Binding of thrombin to fibrin derived from recombinant (rh-Fbg) and human plasma fibrinogen (h-Fbg). Both rh-Fbg and h-Fbg were isolated via GPRP-affinity chromatography and 0.5 mg/ml (final concentration) was incubated for 30 min at 37° C. with various concentration of thrombin. Clots were spun down by centrifugation and the remaining thrombin activity was measured by the S-2238 substrate.

Figure 14A:
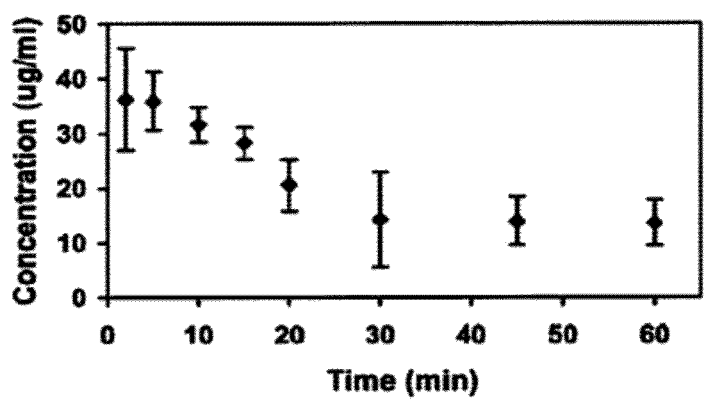

FIGS. 14A, B: Clearance of test (A) and control (B) substances.

DETAILED DESCRIPTION

The following terms and definitions are to be understood as follows.

A bleeding episode refers to a period characterized by bleeding in a patient, which is preceded and followed by longer periods without bleeding.

A known risk of bleeding means a patient is at a higher risk than the general population of bleeding either by knowledge of subsequent exposure to a particular event or because the patient has an inherited or acquired condition that predisposes the patient to bleeding episodes.

Natural human fibrinogen means fibrinogen derived from human plasma. Although such fibrinogen can be purified sufficiently for pharmaceutical use, it contains trace amounts of other human proteins.

Recombinant fibrinogen means fibrinogen expressed from recombinant construct in cell culture, a transgenic animal or in vitro. Unless otherwise apparent from the context recombinant fibrinogen means recombinant human fibrinogen or from fibrinogen from other mammals. Recombinant fibrinogen expressed in nonhuman cells or a nonhuman animal or in a nonhuman in vitro expression system can be made completely free of other human proteins. Recombinant fibrinogen can also be entirely free of pathogens that may be present in human plasma.

Total plasma concentration of fibrinogen refers to the sum of the concentration of administered fibrinogen and endogenous fibrinogen.

A patient typically means a human but can include other mammals, such as horses, dogs, cats, sheep, pigs, mice and rats.

Low half-life fibrinogen means fibrinogen having a reduction in half-life (i.e., reduced beyond a margin of experimental error inherent in measuring half-life) relative to natural human fibrinogen in the same assay. The half-life of natural human fibrinogen in humans is about 3 days.

Under-sialyated fibrinogen means fibrinogen having a reduced sialic content relative to natural human fibrinogen. Natural human fibrinogen has a sialic content of about 7.7 mole sialic acid per mole fibrinogen.

Endogenous fibrinogen means fibrinogen naturally circulating in the plasma of a patient as distinct from exogenous fibrinogen, which is administered to a patient.

The invention provides methods of treating or effecting prophylaxis of bleeding using fibrinogen having reduced half-life relative to natural plasma fibrinogen (low half-life fibrinogen). The methods are premised in part on the result that recombinant human fibrinogen can be expressed in a substantially under-sialylated form. This form of fibrinogen has a reduced half-life relative to natural human fibrinogen but has similar or improved clotting activity. Some of the disclosed methods are further premised in part on the insight that a reduced half-life is often advantageous in treating or effecting prophylaxis of bleeding. Many diseases have a chronic nature in which long-term maintenance of steady state levels of a therapeutic is required. In such disorders, therapeutics with long half-lives are advantageous in reducing dosing frequency. By contrast, bleeding often has an acute nature. Such is particularly evident when bleeding occurs as a result of a specific event, such as trauma or surgery, but is also the case in longer term bleeding disorders in which episodes of bleeding are interspersed between periods in which no bleeding occurs. In such situations, low half-life fibrinogen is advantageous because the fibrinogen can be administered when required to treat or effect prophylaxis of bleeding and rapidly clears from the circulation, decreasing the risk of side effects when the fibrinogen is no longer needed. Such administration offers an improved efficacy to side effects profile relative to that of natural human fibrinogen.

Production of Recombinant Fibrinogen

Fibrinogen is a complex protein consisting of three different chains, α, β and γ, all occurring twice in the total complex. Fibrinogen includes natural human fibrinogen isolated from human plasma or recombinant human fibrinogen. Typically, the chains of recombinant fibrinogen are a natural human sequence but truncated or mutated forms having at least 90 or 95% sequence identity with natural human forms and retaining functional activity (i.e., clotting activity) can also be used. The three genes encoding these chains are 6.7, 7.6 and 8.4 kb respectively, and all lie within a 50 kb region on chromosome 4q28. The α-gene lies behind the γ-gene and is transcribed in the same direction as the γ-gene, whereas the β-gene, which lies downstream of the α-gene, is transcribed in the opposite direction. Each of the fibrinogen chains includes a signal sequence that is cleaved in the course of posttranslational processing and secretion.

Production of biologically active recombinant fibrinogen has been widely described in the scientific and patent literature. For example, recombinant fibrinogen has been produced in human embryonic kidney cells (WO2007/103447), in yeast (WO96/07728), COS cells and other eukaryotic cells (U.S. Pat. No. 6,037,457, EP 1661989). Production of biologically active recombinant fibrinogen has also been achieved in the milk of several transgenic animals, including mice, sheep and cattle (Garner et al., WO95/23868, Velander et al., WO95/22249; Prunkard et al., Nature Biotech 14, 867-71 (1996) and Butler et al. Transgenic Research 13, 437-50 (2004), US 2007219352 and WO00/17239).

For transgenic expression, transgenes are preferably designed to target expression of a recombinant fibrinogen to the mammary gland of a transgenic non-human mammal harbouring transgene(s) encoding the three fibrinogen chains. The basic approach entails operably linking an exogenous DNA segment encoding a fibrinogen chain including a signal sequence, and a regulatory sequence effective to promote expression of the exogenous DNA segment. Typically, the regulatory sequence includes a promoter and enhancer. The DNA segment can be genomic, minigene (genomic with one or more introns omitted), cDNA, and a YAC fragment. Inclusion of genomic sequences generally leads to higher levels of expression.

Regulatory sequences such as a promoter and enhancer are from a gene that is exclusively or at least preferentially expressed in the mammary gland (i.e., a mammary-gland specific gene). Preferred genes as a source of promoter and enhancer include beta-casein, kappa-casein, alphaS1-casein, alphaS2-casein, beta-lactoglobulin, whey acid protein, and alpha-lactalbumin. The promoter and enhancer are usually but not always obtained from the same mammary-gland specific gene.

Transgenes are introduced into non-human mammals. Most non-human mammals, including rodents such as mice and rats, rabbits, ovines such as sheep, caprines such as goats, porcines such as pigs, and bovines such as cattle and buffalo, are suitable. Bovines offer an advantage of large yields of milk, whereas mice offer advantages of ease of transgenesis and breeding. Rabbits offer a compromise of these advantages. A rabbit can yield 100 ml milk per day with a protein content of about 14% (see Buhler et al., Bio/Technology 8, 140 (1990)) (incorporated by reference in its entirety for all purposes), and yet can be manipulated and bred using the same principles and with similar facility as mice. Nonviviparous mammals such as a spiny anteater or duckbill platypus are typically not employed. In some methods of transgenesis, transgenes are introduced into the pronuclei of fertilized oocytes (WO 91/08216). Alternatively, transgenes can be introduced into embryonic stem cells. Transgenic animals can also be produced by methods involving nuclear transfer (WO 97/07669, WO 98/30683, WO 98/37183, WO 98/39416, WO 99/37143).

Analogous strategies can be used to produce fibrinogen in other bodily fluids of transgenic animals (e.g., urine or blood) or in transgenic plants or plant seeds. Regulatory sequences are selected appropriate for the cell type in which expression is intended. For example, the promoter from the uroplakin gene is suitable for expression in urine. Fibrinogen chains' natural promoters or promoters from coagulation proteins such as protein C or Factor VIII are suitable for expression in blood.

In general, similar strategies can be used for expression in cell culture except that there is usually more flexibility regarding choice of promoter and introduction into cells is simpler. Microbes, such as yeast, are one useful system. *Saccharomyces* is a preferred host, with suitable vectors having expression control sequences, such as promoters, including 3-phosphoglycerate kinase or other glycolytic enzymes, and an origin of replication, termination sequences and the like as desired. Insect cells in combination with baculovirus vectors can also be used.

Mammalian tissue cell culture can also be used to express and produce biologically active fibrinogen. A number of suitable host cell lines capable of secreting intact immunoglobulins have been developed including CHO, Cos, HeLa, PER.C6® cells and myeloma cell lines. Expression vectors for these cells can include expression control sequences, such as an origin of replication, a promoter, and an enhancer, and necessary processing information sites, such as ribosome binding sites, RNA splice sites, polyadenylation sites, and transcriptional terminator sequences. Suitable expression control sequences include promoters derived from immunoglobulin genes, SV40, adenovirus, bovine papilloma virus, or cytomegalovirus.

Irrespective of the expression system or purification method, recombinant fibrinogen is typically purified from its environment (e.g., milk or cell culture). Several methods for purification of fibrinogen have been described (EP1115742; EP1115745 describing methods of purification by cation exchange and hydrophobic interaction chromatography respectively). Fibrinogen can also be purified by ethanol precipitation or affinity chromatography as discussed in the Examples.

Recombinant fibrinogen is prepared with reduced glycosylation, and in particular reduced sialylation, compared with natural human fibrinogen from plasma. The level of sialyation of plasma fibrinogen is about (i.e., within a margin or error inherent in measurement) 7.7 mole sialic acid per mole fibrinogen. Thus, under-sialyated fibrinogen is characterized by about 0-7 mole sialic acid per mole fibrinogen, and preferably 0-1, 0-2, 0-3, 0-4, 0-5, 0-6 or 1-2 mole sialic acid per mole fibrinogen. Most preferred is a sialic acid content that still renders the protein active but with a lower half life than the natural human fibrinogen. As shown in the Examples, the reduction in sialyation can be the result of recombinant expression without further manipulation in vitro. Under sialyation has also been reported in other proteins expressed in cell culture or transgenically. Alternatively or additionally recombinant fibrinogen can be subject to desialyation by enzymatic or chemical treatment as described further below.

Under-sialyation results in increased clearance via specific receptors in the liver and consequently decreased half-life, because the desialylated glycoproteins are recognised by various carbohydrate receptors in the body (Morell et al. (1971) J. Biol. Chem. 246, 1461). A relative reduction in half-life between under-sialyated fibrinogen and natural fibrinogen can be shown by pharmacokinetic studies in an animal model as disclosed in the Examples. However, absolute half-lives of a human protein in a human are usually longer than those in an animal model because in an animal model the human protein is subject to an immune response against a non-self protein that would not be present in a human The normal half-life of human plasma fibrinogen when reintroduced into human plasma is about three days. The half-life of under-sialyated recombinant fibrinogen is shorter than that of human plasma. The extent of shortening depends on the extent of under-sialyation but can be less than 75%, 50% or 25% of natural human fibrinogen. Optionally, under-sialyated human fibrinogen has a half-life that is 10-75% of that of natural human fibrinogen and sometimes 20-50% of natural human fibrinogen in humans. Optionally, under-sialyated human fibrinogen has a half-life in humans of less than 2 days, less than 1 day, or less than 12 hours.

Plasma Fibrinogen

Natural human fibrinogen isolated from plasma is commercially available from several sources, including Baxter, Aventis, Alpha Therapeutics, Innovative Research and Sigma Aldridge. Such fibrinogen is extensively glycosylated having about 7.7 mol sialic acid per fibrinogen molecules, and has a plasma half-life of about three days. The sialic acid residues can be removed by either enzymatic or chemical treatment. For enzymatic treatment, the preferred enzyme is sialidase 1 also known as neuraminidase. The enzyme is commercially available from various commercial suppliers (e.g., New England Biolabs, Sigma Aldrich) and various origins (e.g., human, *arthrobacter ureafaciens* and *Clostridium perfringens*). Neuraminidase is capable of cleaving all non-reducing unbranched N-acetylneuraminic and N-glycolylneuraminic acid residues and also cleaves branched sialic acids at higher concentrations of enzyme and prolonged incubations. Desialyation can also be performed with acid hydrolysis. For example, trifluoromethanesulphonic acid (Edge, et al. (1981) Anal. Biochem. 118, 131-137) has been used extensively to remove carbohydrate from glycoproteins, while leaving the protein backbone intact. Exemplary conditions for chemical and enzymatic treatment are well described in the manufacturers' instructions and scientific literature. However, initial titrations with different durations of treatment or concentrations of reagents are recommended to achieve desired levels of desialyation (e.g., similar to those shown in the present examples). Optionally, the sialyation level can be reduced to an average of less than 5, 4, 3, 2, or 1 molecules of sialic acid per mol of fibrinogen. Optionally, the sialic content is 0-3 or 0-2 moles sialic acid per mole of fibrinogen. Although not necessary further deglycosylation can be performed after removal of sialic acid residues using other deglycosylates, such as PNGase F, B-Galactosidase, Glucosaminidase, and O-Glycosidase, all available from QA Bio.

Bleeding Conditions

The methods and uses of the invention are useful in treating or effecting prophylaxis of a wide variety of conditions characterized by bleeding, regardless of etiology. Such conditions include bleeding as a result of trauma (e.g., car crash, battlefield, sports), bleeding as a result of surgery (e.g., orthopedic surgery, organ transplant surgery, cardiovascular surgery, biopsy, dental procedures). Such conditions also include bleeding as result of organ failure (e.g., kidney, heart, or liver failure). Increased propensity for bleeding can also be caused by transfusion of plasma or fluids, which effectively dilutes endogenous coagulation factors or may exert direct effects on the coagulation system. Such diseases also include hereditary or acquired conditions characterized by a deficiency in fibrinogen or any other molecule involved in blood coagulation. Such a deficiency may be the result of relative lack of such a molecule or presence of normal amounts of such a molecule but of diminished function. Bleeding conditions can also result from vascular defects, thrombocytopenia and thombocytopathia, or excessive fibrinolytic activity. Some examples of bleeding conditions include hemophilia, Hypoprothrombinemia, von Willebrand's disease, Glanzman's thrombasthenia, Soulier Disease, and Factor XI deficiency. Bleeding is sometimes also sometimes due to unknown causes, as in the case of idiopathic or iatrogenic bleeding.

In some of the conditions discussed above, such as trauma or surgery, the bleeding typically occurs as an acute condition and, if appropriately treated, may never recur. In other conditions, such as those characterized by deficiencies in a coagulation molecule, bleeding episodes recur periodically through a patient's life but can often by interspersed by relatively long periods without bleeding. Although in some of the above conditions (e.g., a car crash), bleeding is unforeseeable and can be treated only after it occurs, in other conditions (e.g., scheduled surgery) bleeding is foreseeable and can be treated prophylactically. Prophylactic treatment can also be useful in patients having chronic bleeding conditions in periods in which no bleeding is present. In all of the above conditions, the plasma levels of fibrinogen may or may not be reduced below normal levels. The invention methods may, therefore, be applied in settings without an absolute fibrinogen deficiency.

Treatment Regimes

The invention provides methods of treatment and uses in which the medicament comprising the fibrinogen with reduced half-life is manufactured and subsequently can be administered to patients who are bleeding (therapeutic treatment) or at known risk of bleeding (prophylaxis). A regime of a dosage, route and intervals of administration that inhibits, reduces or terminates bleeding, and/or increases the speed or strength of clot formation and/or increases survival in a patient who is bleeding is referred to as a therapeutically effective regime. A regime of a dosage, route of administration and intervals of administration that delays the delays, inhibits and/or prevents bleeding in a patient at known risk of bleeding is referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a clinical trial in a population of treated patients relative to a control population of untreated patients.

Low half-life fibrinogen can be used in any of the applications of natural fibrinogen and may also be used in other applications where natural fibrinogen is not applied. However, preferably the relative half-lives of low half-life and natural fibrinogen are taken into account in determining the dose and frequency of administration of low half-life fibrinogen. In some methods, low half-life fibrinogen is administered in a regime that achieves a higher peak plasma concentration of fibrinogen (recombinant plus endogenous plasma fibrinogen) than would normally be employed with natural fibrinogen but with a faster return to normal or below normal values of fibrinogen (recombinant plus endogenous plasma fibrinogen). The high initial peak concentration is advantageous in obtaining a rapid and strong response in treating what is often an acute, and sometimes life-threatening condition. A rapid decline in concentration is advantageous in resulting in removal of excess fibrinogen after it has played its therapeutic role, reducing the potential for side effects due to excess fibrinogen, such as thrombosis, stroke, heart attack or ischemia. Alternatively, but less preferably, low half-life fibrinogen can be employed at similar dosages and peak concentrations as natural fibrinogen, but administered at more frequent intervals than natural fibrinogen such that the area under the curve (AUC) for low half-life fibrinogen and natural fibrinogen are similar as is patient response to treatment.

The normal plasma volume in an adult human is about 3 L, and the normal concentration of plasma fibrinogen is about 2-4 g/L. Thus, each three grams of low half-life fibrinogen increases the plasma concentration by about 1 g/L. In patients being treated or prophylaxed, the initial level of plasma fibrinogen is often below normal levels but can also be within or even about normal levels. If the level of plasma fibrinogen is measured before commencing treatment, the dose of administered low half-life fibrinogen can be adjusted to achieve a desired effect on total plasma concentration of fibrinogen. In some methods, the dose is adjusted so the peak concentration of total fibrinogen is within normal levels. In other methods, the dose is adjusted so that the peak concentration of total fibrinogen is above normal levels. In some methods, the dose can be adjusted to achieve a peak level of total plasma fibrinogen of 2-15 or 2-12 g/L. In some methods and uses according to the invention, the dose is adjusted to achieve a peak level of total plasma fibrinogen of greater than 1, 2, 3, 4, 5, 6, 7, 8, 9, 10, 11, 12, 13, 14 or 15 g/L. In some methods, the dose is adjusted to achieve a peak level of total plasma fibrinogen of 4-12 g/L, 6-12 g/L, 8-12 g/L, 4-15 g/L, 6-15 g/L or 8-15 g/L. In some methods, the dosage is such as to confer a peak level of low half-life fibrinogen of 1-12 g/L or 1-15 g/L. In some methods, the dose is such as to confer a peak level of low half-life fibrinogen of greater than 1, 2, 3, 4, 5, 6, 7, 8, 9, 10, 11, 12, 13, 14 or 15 g/L. In some methods, the dose is adjusted to achieve a peak level of low half-life fibrinogen of 4-12 g/L, 6-12 g/L, 8-12, 4-15, 6-15 or 8-15 g/L. In some methods, the dose of low half-life fibrinogen is 1-12 or 1-15 g, or 1-3, 3-6, 6-9 or 9-12 g. In some methods, the dose of low half-life fibrinogen is at least 1, 2, 3, 4, 5, 6, 7, 8, 9, 10, 11, 12, 13, 14 or 15 g.

Low half-life fibrinogen can be administered in single or multiple doses to a patient. In some methods, a single dose is administered per bleeding episode, or multiple doses are administered within a relatively short period of time, such as a day, 6 hours or 2 hours per bleeding episode. The administration of a single dose or multiple doses within a short period is particularly useful in regimes in which the maximum peak concentration of total fibrinogen is raised to normal or above normal levels. The administration of a single dose or multiple closely spaced doses in combination with the low half-life leads to a more rapid return to normal or below normal levels of fibrinogen and reduced potential for side effects from continued presence of administered fibrinogen after the desired effects of treatment or prophylaxis have been achieved. Thus, some such regimes are characterized by a peak concentration of total plasma fibrinogen higher than would be sought using plasma fibrinogen as a therapeutic agent, but with a more rapid decline to normal or below normal levels of total plasma fibrinogen than would result from a conventional regime of plasma fibrinogen.

In other methods, particularly useful in therapeutic treatment or prophylaxis of chronic conditions, low half-life fibrinogen is administered on multiple occasions for extended periods (e.g., a week or a month). In such regimes, the low half-life fibrinogen can be administered more frequently than would be the case with plasma fibrinogen to maintain a similar mean plasma total fibrinogen content and similar therapeutic or prophylactic activity to plasma fibrinogen. The interval of dosing for maintaining approximately steady state levels of low half-life fibrinogen can be from about 1-3 times the half-life of low half-life fibrinogen. In some methods, levels of total plasma fibrinogen are monitored, and additional dose(s) of low half-life fibrinogen are administered responsive to a decline in plasma concentration below a desired level (e.g., below 2, 3, 4, 5, 6, 7, 8, 9, 10, 11 or 12 g/L).

Low half-life fibrinogen can be administered with or without other treatments for bleeding. Such other treatments include other proteins involved in coagulation, such as factor VIIa, and factor VIII, von Willebrand's factor, Desmopressin, first aid including applying bandages or tourniquets, transfusion and surgery to close wounds. Low half-life fibrinogen is particularly useful when administered within one hour after bleeding starts. During this period, other treatments, particularly surgery to close wounds, may not be available. If appropriate, surgery to close wounds can be performed as soon as practical after administering low half-life fibrinogen.

In some methods, plasma concentration of fibrinogen is determined before and/or after administration of low half-life fibrinogen. Total plasma fibrinogen content can be measured by an ELISA among other methods. Low half-life and natural fibrinogen concentrations can be measured separately by ELISA using antibodies specific for the respective forms or one antibody specific for one form in combination with an antibody binding to both forms. Low half-life and natural fibrinogen can also be distinguished by HPLC as discussed in the Examples.

The invention relates to a pharmaceutical composition comprising human fibrinogen having reduced half-life relative to natural plasma fibrinogen, and a pharmaceutically acceptable carrier. In a preferred embodiment, said human fibrinogen has a sialic acid content of 0-2 moles sialic acid per mole fibrinogen.

The invention also relates to the use of fibrinogen having a reduced half-life relative to natural human plasma fibrinogen in the manufacture of a medicament for the treatment or prophylaxis of bleeding in a patient who is bleeding or is at risk of bleeding. Preferably, said fibrinogen is under-sialyated. Said fibrinogen is recombinant human fibrinogen or isolated/derived from plasma.

In a preferred embodiment, the invention relates to said use, wherein the half-life is reduced by a factor of at least 50% relative to that of human plasma fibrinogen, and preferably wherein the half-life is less than one day. Preferably, the dose is greater than 1 g as outlined above. In another preferred embodiment of the invention, the dose delivers a peak plasma concentration of recombinant and endogenous fibrinogen greater than 2 g/L, as outlined above. Preferably, the peak plasma concentration of recombinant fibrinogen is greater than 1 g/L. In another preferred aspect, the bleeding results from an acute disorder, a traumatic injury, surgery, or an inherited or acquired disorder, such as an inherited or acquired deficiency in a coagulation protein.

The invention also relates to the use of fibrinogen having a reduced half-life relative to natural human plasma fibrinogen in the manufacture of a medicament for the treatment or prophylaxis of bleeding in a patient who is bleeding or is at risk of bleeding, wherein the treatment is in a regime sufficient to achieve a peak concentration of fibrinogen in plasma including administered and endogenous fibrinogen that is within or above normal levels, and wherein the plasma concentration declines to normal or below normal levels within three days of first administration. Preferably, the peak plasma concentration of fibrinogen including administered and endogenous fibrinogen is above 2 g/L. In another preferred embodiment, the peak plasma concentration of fibrinogen including administered and endogenous fibrinogen is within 2-4 g/L and the plasma concentration of fibrinogen declines below 2 g/L within one day. In another aspect of the invention, the regime is such that fibrinogen is administered once or at multiple times occurring within a period of no more than two hours. Preferably, the regime is such that fibrinogen is administered multiple times at intervals no greater than two days.

Pharmaceutical Compositions and Routes of Administration

Low half-life fibrinogen or pharmaceutical compositions containing the same are usually administered parenterally with intravenous, intraarterial, or subcutaneous administration being preferred.

Low half-life fibrinogen is often administered with one or more other pharmaceutically acceptable components as a pharmaceutical composition. See Remington's Pharmaceutical Science (15th ed., Mack Publishing Company, Easton, Pa., 1980). The preferred form depends on the intended mode of administration and condition of the patient. The compositions can also include, depending on the formulation desired, pharmaceutically-acceptable, non-toxic carriers or diluents, which are defined as vehicles commonly used to formulate pharmaceutical compositions for animal or human administration. The diluent or pharmaceutically acceptable carrier is selected so as not to affect the biological activity of the combination. Examples of such diluents/carriers are distilled water, physiological phosphate-buffered saline, Ringer's solutions, dextrose solution, and Hank's solution. In addition, the pharmaceutical composition can include protease inhibitors. The pharmaceutical compositions can also include divalent metal cation ions, which have been reported to improve stability (see U.S. Pat. No. 7,045,601). Additionally, auxiliary substances, such as wetting or emulsifying agents, surfactants, pH buffering substances and the like can be present in compositions. Chelating agents, such as citrate or EDTA can also be included. Other components of pharmaceutical compositions can include animal, vegetable, or synthetic origin, for example, peanut oil, soybean oil, and mineral oil.

Compositions can be prepared as lyophilized powders for reconstitution prior to use or in liquid solution or suspension. Compositions can be stored frozen, on ice or at room temperature.

The low half-life fibrinogen incorporated in such compositions is typically substantially pure, e.g., at least 85, 95 or 99% w/w pure from undesired contaminants.

EXAMPLES

Example 1

Production of Recombinant Fibrinogen

Figure 1:
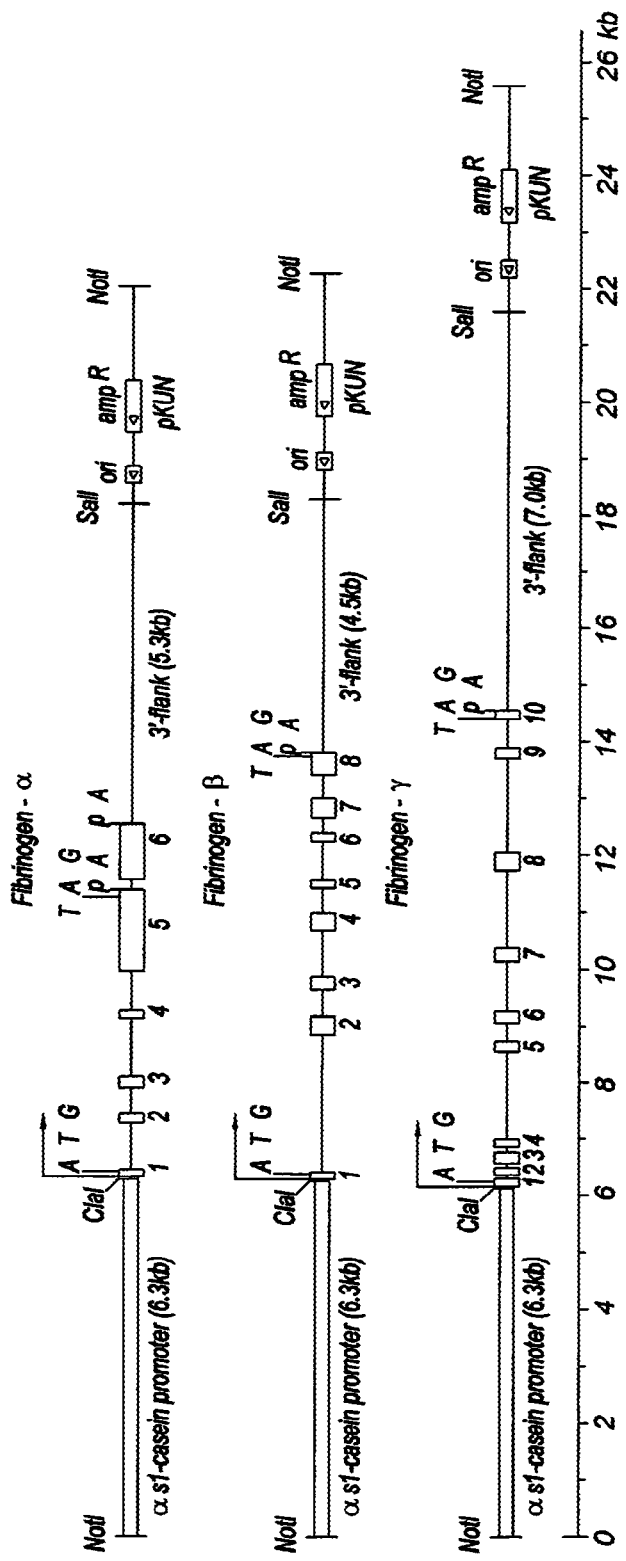
FIG. 1 shows three genomic expression vectors were constructed containing the α-, β- or γ-gene under control of the αS1-casein promoter.
Figure 2:
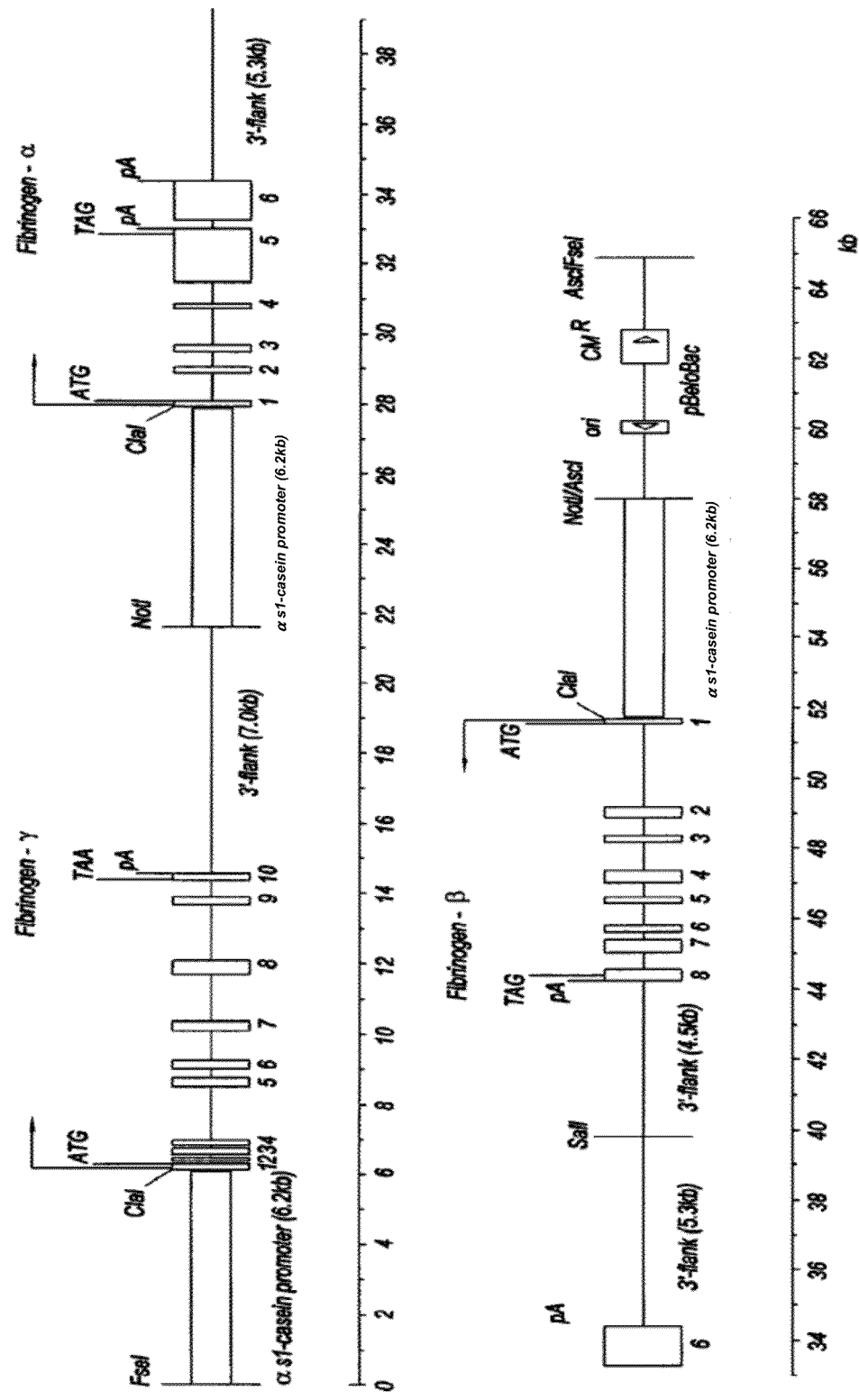
FIG. 2 shows a further exemplary vector was generated by combining the three α-, β and γ-fibrinogen constructs in one vector (FIB3 construct). Transgenic cows have been generated from both types of vector. Expression levels have ranged from about 1-3 mg/ml in different lines.

FIG. 1 shows three genomic expression vectors were constructed containing the α-, β- or γ-gene under control of the αS1-casein promoter. FIG. 2 shows a further exemplary vector was generated by combining the three α-, β and γ-fibrinogen constructs in one vector (FIB3 construct). Transgenic cows have been generated from both types of vector. Expression levels have ranged from about 1-3 mg fibrinogen/ml milk in different lines.

Example 2

Purification of Recombinant Fibrinogen from Bovine Milk

To compare recombinant fibrinogen (rh-Fbg) to natural human fibrinogen, both recombinant human fibrinogen, expressed in bovine milk, and human fibrinogen from human plasma has been purified via a similar purification process. For the purification of recombinant fibrinogen (rh-Fbg), milk production was hormonally induced in a transgenic cow (cow 204; Fay), collected twice a day and stored at below −18° C. until further processing. At the start of the purification, milk was thawed and caseins and fat were removed by high speed centrifugation. Next, ε-Amino-caproic acid (ε-ACA) was added to prevent degradation of the fibrinogen by various proteases present in milk and plasma and subsequently, the whey (milk without caseins and fat) was subjected to ethanol precipitation. The precipitate was collected by centrifugation, washed, dissolved and subjected to another ethanol precipitation step in the absence of c-ACA. Finally, the pellet was dissolved in 20 mM sodium citrate pH 7.0, 0.15 M NaCl buffer, filtered over a 0.45 lam filter and stored at below −50° C. The same procedure was followed for human plasma-derived fibrinogen (h-Fbg). In addition, for both fibrinogen resources, the procedure has been performed in the absence of c-ACA.

Example 3

Structural Characterization of Fibrinogen

Figure 3:
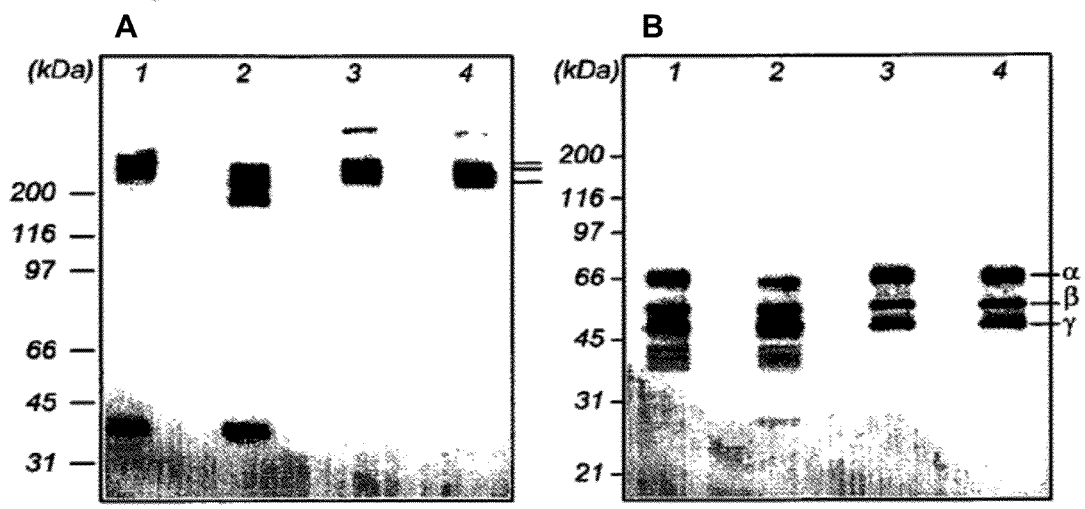
FIGS. 3 A, B: Non-reduced and reduced SDS-PAGE showing recombinant- and plasma-derived fibrinogen. Both recombinant (rh-Fbg) and human plasma fibrinogen (h-Fbg) were isolated in the absence or presence of ϵ-ACA and subjected to SDS-PAGE (4-20%) analysis. The proteins were visualized by silverstaining. Non-reduced (left panel) and reduced (right panel) SDS-PAGE: Lane 1 and 3: rh-Fbg and h-Fbg, respectively purified in the presence of c-ACA. Lane 2 and 4: rh-Fbg and h-Fbg, respectively purified in the absence of c-ACA. Arrows on the right of the left panel indicate the HMW, LMW and LMW' fraction. Molecular weight markers are indicated at the left.

Human plasma fibrinogen appears heterogeneous by SDS-polyacrylamide gel electrophoresis (SDS-PAGE) and other methods for separation of proteins by molecular size. Full size, undegraded fibrinogen has a molecular weight of 340 kD (HMW-fibrinogen) and accounts for approximately 50%-70% of total fibrinogen. A second degraded form with a molecular weight of 305 kD (LMW) accounts for about 20-40% of total fibrinogen and the residual amount is LMW'-fibrinogen with a molecular weight of 280 kD. The two degraded forms differ in their Act-chains i.e. the LMW misses one of the two Aα-chains, whereas both Aα-chains are lacking in the LMW' form, Holm, 1985, *Thromb Res* 37:165. Both rh-Fbg and h-Fbg were analyzed by SDS-PAGE and revealed that rh-Fbg is very similar to purified h-Fbg (FIG. 3). Under non-reducing conditions and in the presence of ε-ACA, both rh-Fbg and h-Fbg display the three characteristic molecular weight bands (HMW, LMW and LMW') of fibrinogen in a similar ratio. However, rh-Fbg contains a 40 kD band, an impurity that is not seen in h-Fbg. In the absence of ε-ACA, the HMW band from rh-Fbg is degraded and reduced SDS-PAGE analysis revealed that the intensity of the α-chain is reduced. This indicates that the degradation resides in the α-keten of rh-Fbg (FIG. 3, right panel, lane 2) and is most likely caused by plasmin. No such degradation was observed in fibrinogen obtained from plasma.

Under reducing conditions, both fibrinogen preparations appear as three predominant bands that correspond to the Aα, Bβ and γ-chains of fibrinogen. However, the recombinant fibrinogen contains an additional triplet below the γ-chains which is not present in plasma-derived fibrinogen. This triplet may be related to the 40 kD impurities observed on non-reduced SDS-PAGE. In addition, an extra protein band became visible above the γ-chain of rh-Fbg and h-Fbg, representing most likely the γ' variant. This variant represents in human plasma the alternative splice variant of the γ-chain that contains two sulfated tyrosins. Chung, 1984, *Biochemistry* 23:4232

Figure 4:
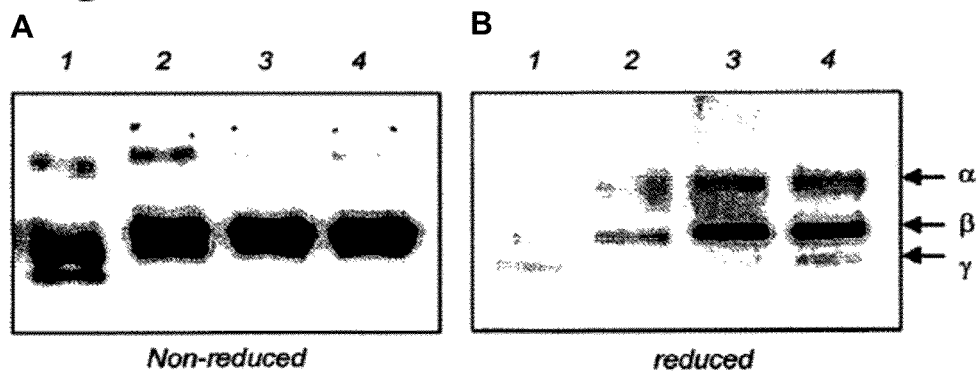
FIGS. 4A, B: Western blot analysis of recombinant and human plasma fibrinogen. Samples were run on a 4-20% SDS-PAGE gel under non-reduced and reduced conditions. Proteins were transferred onto nitrocellulose and the blot was incubated with an anti-fibrinogen antibody. Lanes 1 and 3 show rh-Fbg and h-Fbg, respectively purified in the absence of G-ACA; lanes 2 and 4 show rh-Fbg and h-Fbg, respectively purified in the presence of G-ACA.

To demonstrate that the different bands observed on SDS-PAGE are indeed derived from fibrinogen bands, their identity was confirmed by western blot analysis. By using a polyclonal antibody that mainly recognizes the α- and β-chains and to a lesser extent the γ-chain, the similarity between rh-Fbg and h-Fbg was confirmed (FIG. 4). As shown by SDS-PAGE, fibrinogen isolated in the absence of ε-ACA misses the α-chain, which is confirmed by western blot analysis.

Based on the appearance on SDS-PAGE and western blot analysis the purity of the recombinant fibrinogen is estimated to be about 85% with main impurities around 40 kD.

This 40 kD impurity was recognized by the anti-fibrinogen antibody indicating that this is a fibrinogen-derived impurity. One possibility is that this impurity is due to plasmin-mediated degradation of fibrinogen. The purity of the plasma, derived fibrinogen was estimated to be 95% with most likely fibronectin as main impurity.

Figure 5:
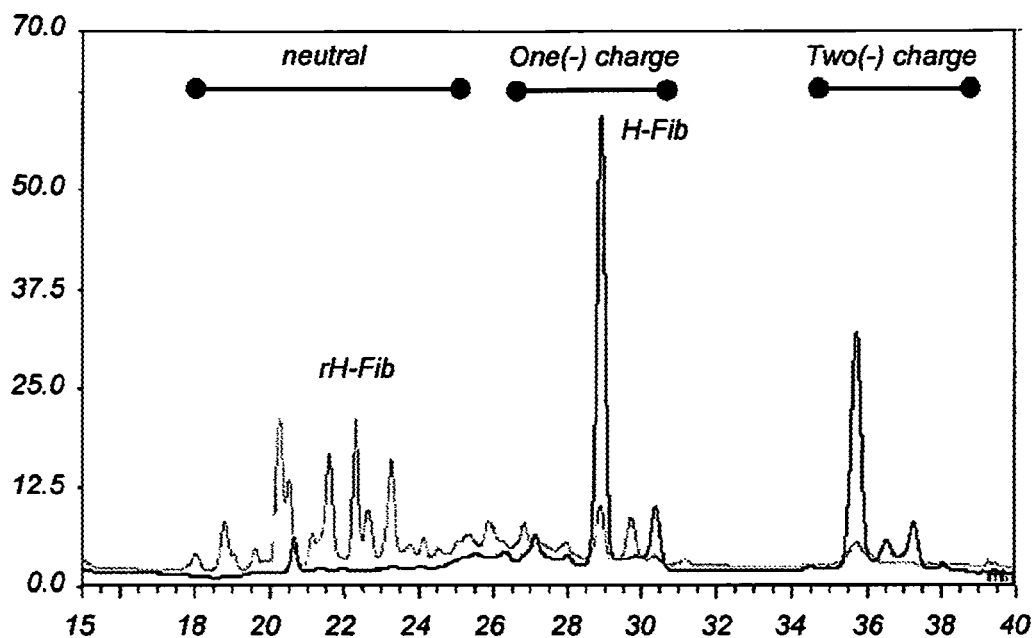
FIG. 5: N-linked glycan profile of recombinant and plasma-derived fibrinogen. Using HPAEC-PAD, the N-linked profile of recombinant fibrinogen (rh-Fbg) and human plasma-derived fibrinogen (h-Fbg) was established and revealed that rh-Fbg contained mainly neutral glycans whereas h-Fbg contained mainly charged sialylated.

Using a high-performance anion-exchange chromatography-pulse amperometric detection (HPAEC-PAD) system, Barroso, 2002, *Rapid Commun Mass Spectrom* 16:1320, the glycosylation of rh-Fbg and h-Fbg was compared. The N-linked glycan profile showed apparent differences in glycosylation between recombinant fibrinogen that contained mainly neutral glycans, whereas plasma-derived fibrinogen contained mainly sialylated glycans (FIG. 5). This difference in glycosylation pattern is commonly seen in eukaryotic recombinant expression systems in which glycoproteins are produced not as a single structural entity but as a set of differently glycosylated variants of the particular polypeptide. The difference in sialylation was confirmed by measuring the sialic acid content of the fibrinogen preparations. For rh-Fbg, this was found to be 1.5 mol/mol, whereas h-Fbg was almost fully sialyated at 7.7 mol/mol. Whether the difference in glycosylation influences the function of the fibrinogen molecule is not known. However, it has been suggested that a decrease in sialic acid increases the rate of fibrin polymerization, Henschen, 1993, *Thromb Haemost* 70:42. (see section 4.1).

Example 4

Functional Characteristics of Recombinant Fibrinogen

A: Polymerization and Clottability of Fibrin Monomers

Fibrinogen is converted into an insoluble fibrin clot in three stages. First, thrombin cleaves the amino-termini of the Aα- and Bβ-chains of fibrinogen, releasing fibrinopeptides A and B, respectively, and converting fibrinogen to fibrin monomers. Next, these fibrils align in a half-staggered overlap and polymerize to form fibrin strands. The final step is a side-toside association of the polymers resulting in the formation of the gel. By using the polymerization assay, the three stages of fibrin formation can be followed by assessing the following three parameters. 1) The lag-phase: this is the time needed to form protofibrils upon the addition of thrombin. 2) gelation rate: This is the slope of the curve which illustrates the speed of fibrin formation and 3) the plateau: this is the maximum OD reached and is related to the average size of fibrin fibers i.e. the higher the plateau, the thicker the fibers.

Figure 6:
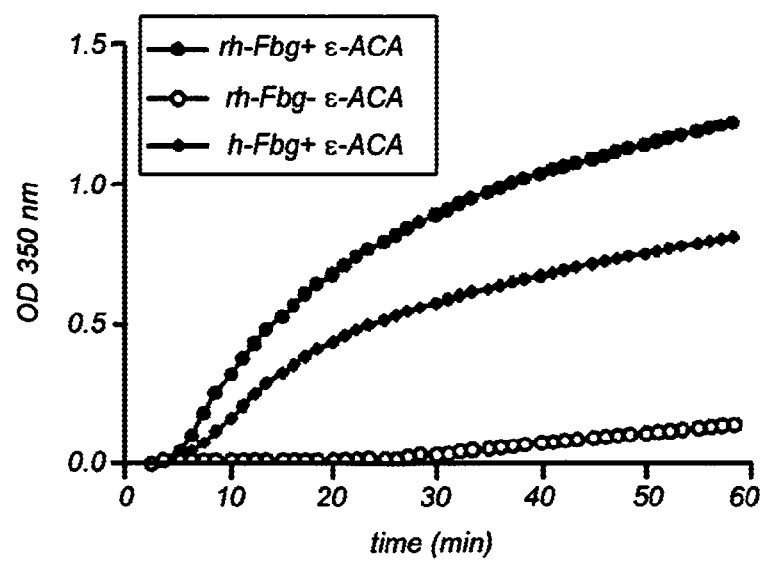
FIG. 6: Polymerization of purified fibrinogen samples. Polymerization was initiated by the addition of thrombin (0.025 U/ml) to both recombinant (rh-Fbg, isolated in the presence or absence of ϵ-Aminoaproic acid (c-ACA)) and plasma fibrinogen (h-Fbg; both 0.5 mg/ml) preparations at time 0. After 3 min of incubation, polymer formation was followed as change in turbidity at 350 nm in time.

The polymerization of the rh-Fbg and h-Fbg was initiated by thrombin and followed in time at 350 nm. As shown in FIG. 6, both rh-Fbg and h-Fbg have a short lag time (~1 min), indicating that both preparations have a similar rate in protofibril formation. However, rh-Fbg has a steeper slope and a higher plateau illustrating that the rate of protofibrils assembly is faster and the fibrils are thicker in rh-Fbg as compared to h-Fbg. In contrast, the rh-Fbg preparation that was isolated in the absence of ε-ACA and showed degradation, hardly shows any polymerization. The difference in fiber thickness observed between rh-Fbg and h-Fbg may be explained by the difference in sialic content between rh-Fbg and h-Fbg (see section 3.1.3) and may have implications for the fibrinogenolysis process. Thicker fibrils bind more tissue plasminogen activator (tPA), which may result in a faster fibrinolytic rate and the clot will dissolve more rapidly, Gabriel, 1992, *J Biol Chem* 267:24259.

Nevertheless, these data demonstrate that rh-Fbg is fully functional and highly comparable with h-Fbg-derived fibrinogen.

To further determine the potency of the fibrinogen preparations, the fibrinogen preparations were incubated with an excess amount of thrombin and the % clottability of the different fibrinogens was compared to a commercial obtained fibrinogen (Enzyme Research Laboratories (ERL)). Whereas the clottability of h-Fbg was comparable with commercial obtained fibrinogen (~95%), the amount of clottable protein present in the recombinant fibrinogen was with 79% considerably lower (Table 1). This is most likely explained by the presence of the 40 kD impurity present in the recombinant fibrinogen preparation (See section 3.1). When the % clottability was corrected for the impurity, the differences between rh-Fbg and h-Fbg are less pronounced (92% vs 94% clottability, respectively).

TABLE 1

Thrombin-mediated clottability of various fibrinogen preparations.

| | % clottability Average ± SD (n = 4) |
|---|---|
| Recombinant fibrinogen | 78.6 (92) ± 0.5 |
| Plasma-derived fibrinogen | 94.3 ± 0.1 |
| Commercial fibrinogen (ERL) | 93.1 ± 0.2 |

All three fibrinogen preparations were incubated with an excess of thrombin (2 U/ml) in the presence of $Ca^{2+}$ for 20 min at 37° C. The clotted material was spun down and the residual protein concentration was determined by measuring the absorbance at OD280 nm. The fraction of clotted protein over total protein was calculated and expressed as % clottability. The numbers between the quotation marks show the % clottability corrected for the impurities present in the preparation. Commercial fibrinogen was obtained from enzyme research labs (ERL).

B. Platelet Aggregation

As a precursor of fibrin formation, fibrinogen plays a major role in hemostatic plug formation but additionally, it functions as an adhesive for platelets. Platelet aggregation is initiated upon binding of fibrinogen to specific sites of the membrane-bound glycoprotein IIb/IIIa ($\alpha_{IIb}\beta 3$) which subsequently results in the formation of interplatelet bridges, Marguerie, 1979, *J Biol Chem* 254:5357. This binding is a precondition for aggregation in vivo.

The ability of recombinant fibrinogen to cause platelet activation was determined and compared to that of plasma-derived fibrinogen. Therefore, platelets were isolated from human platelet rich plasma (PRP) by gel-filtration and pre-incubated with different concentrations of the various fibrinogens. Platelet aggregation was triggered by the addition of adenosine diphosphate (ADP). ADP binds to its receptor on the platelet surface, which initiates aggregation, exposure of fibrinogen receptors, and calcium mobilization. The results show that rh-Fbg supports blood platelet aggregation to a almost similar extent as observed for plasma-derived fibrinogen. The mean values of rh-Fbg induced platelet aggregation showed only 10-15% smaller aggregation as compared to plasma fibrinogen. This is most likely explained by the impurity present in the recombinant fibrinogen preparation, since comparable results are obtained when the results are corrected for this impurity. Plasma-derived fibrinogen supported platelet aggregation to a similar extent as human fibrinogen (ERL), which was used as a control (Table 2).

TABLE 2

ADP-induced platelet aggregation in the presence of different concentrations of fibrinogen.

| | Extent of ADP-induced blood platelet aggregation (%) | | |
|---|---|---|---|
| | Fbg (200 µg/ml) | Fbg (100 µg/ml) | Fbg (50 µg/ml) |
| Recombinant Fibrinogen | 38 ± 9 | 27 ± 7 | 18 ± 4 |
| Plasma-derived Fibrinogen | 43 ± 10 | 32 ± 6 | 20 ± 4 |
| Human Fibrinogen | 47 ± 7 | nd | Nd |

Platelets were isolated from human platelet rich plasma (PRP) by gelfiltration (Sepharose 4B) in the presence of apyrase. Next, platelets ($2-3 \times 10^8$ cells/ml; 0.5 mL) were preincubated with different concentrations of the various fibrinogens for 2 min at 37° C. in an aggregometer (Chrono-Log, Havertown, PA) under constant stirring. Platelet aggregation was triggered by the addition of adenosine diphosphate (ADP; 5 µM).
nd = not done.

C: FXIII-Mediated Cross-Linking

In addition to fibrinogen, also Factor XIII (FXIII) plays an important role in the regulation of the blood coagulation system. Factor XIII is activated by thrombin, which results in the formation of the transglutaminase FXIIIa. This enzyme stabilizes, in the presence of calcium, the fibrin clot via covalent cross-links between fibrin molecules. Furthermore, it protects the fibrin from degradation by plasmin. Muszbek, 1996, *Crit Rev Clin Lab Sci* 33:357. The basic mechanism of FXIIIa-mediated fibrin cross-linking involves both the α- and γ-chains, but not the β-chains, of fibrin. Activated FXIIIa introduces a number of cross-links between the γ-chains of two neighboring fibrin monomers followed by the cross-linking of the α-chains. This latter process occurs more slowly and results in the formation of highly cross-linked α-chain polymers. In addition to fibrin, also fibrinogen can be cross-linked by FXIII. This reaction follows the same pattern as described for fibrin cross-linking, although at a slower rate, Sidelmann, 2000, *Semin Thromb Hemost* 26:605, and also results in the formation of a clot. The FXIIIa catalyzed cross-linking of fibrin was examined for both the fibrinogen preparations (recombinant and plasma) and compared with commercial obtained plasma-derived fibrinogen. All fibrinogen preparations were incubated with thrombin in the presence or absence of FXIII for 5 min, and the reaction products were analyzed by reduced SDS-PAGE. Furthermore, bands were analyzed by densitometric analysis and % dimerization was calculated according to the following formula: %

Figure 7:
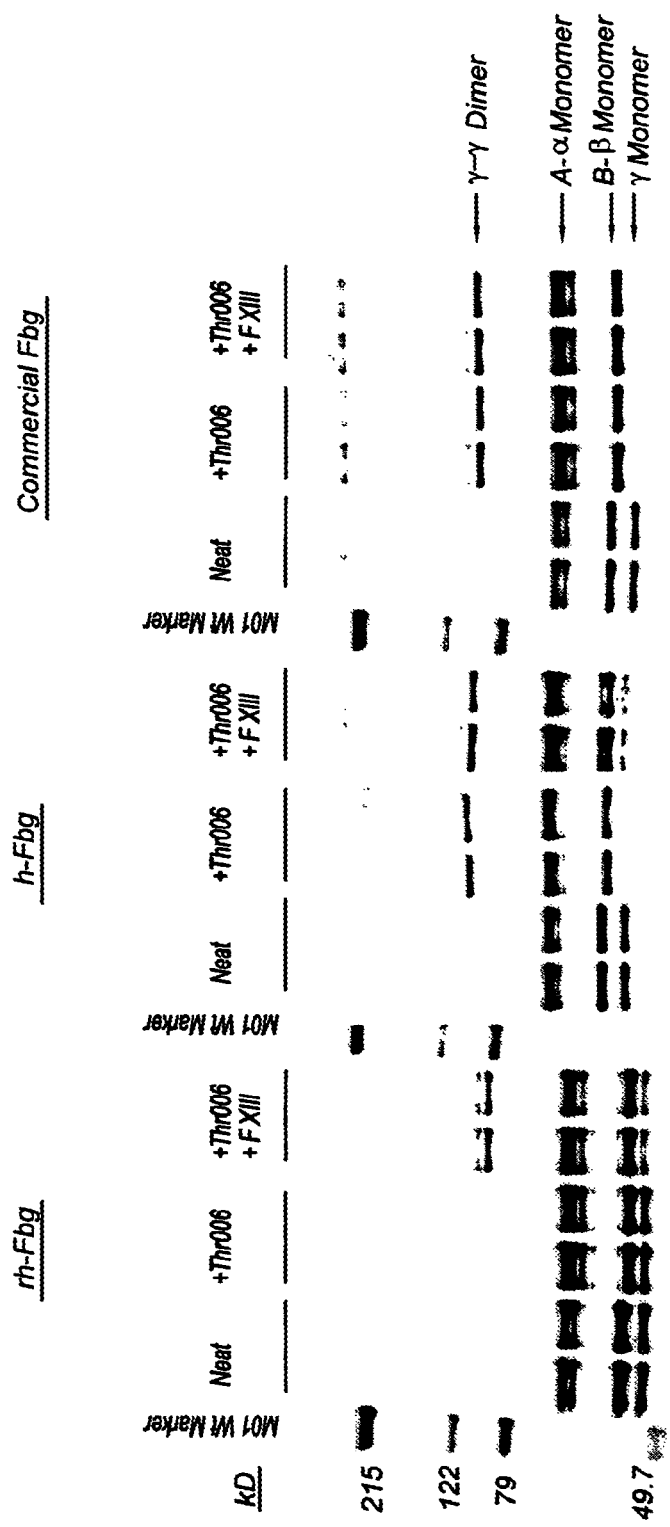
FIG. 7: Factor XIIIa-catalyzed cross-linking of various fibrinogens. Recombinant fibrinogen (rh-Fbg), plasma fibrinogen (h-Fbg) and commercial obtained plasma-derived fibrinogen (commercial-Fbg), all in a final concentration of 8 mg/ml were incubated with thrombin (330 U/ml) and $Ca^{2+}$ (25 mM/ml) for 5 min with or without FXIIIa (2 U/ml). Samples were dissolved and run under reducing conditions on a 8% SDS-PAGE.

Dimerization=γγ-dimer/(γγ-dimer+γ-monomer). As shown in FIG. 7, all three fibrinogen preparations showed γγ-dimerization upon incubation with FXIIIA, that was accompanied by a reduction of the α- and γ-monomer bands. However, γγ-dimerization (and the accompanied reduction of the γ-monomer band) was less pronounced in the rh-Fbg preparation as compared to both plasma-derived preparations (Table 4). The reason for this may reside in the presences of FXIII, as impurity, in plasma derived preparations as both preparations showed already γγ-dimer formation without addition of FXIII. Apparently, the amount of residual FXIII, which was determined by photometric analysis (Table 3) in both plasma-derived fibrinogens, is already sufficient for complete γγ-dimer formation.

TABLE 3

γγ-dimer formation of fibrinogen derived from various origins.

| | Dimerization (%) | | | Residual |
|---|---|---|---|---|
| | neat | +thrombin | +thrombin & FXIII | FXIII (U/mg) |
| Recombinant Fbg | 0.0 | 0.0 | 62.2 | 0.00 |
| Plasma-derived Fbg | 0.0 | 99.6 | 75.6 | 0.25 |
| Commercial H-Fbg | 0.0 | 99.6 | 99.4 | 0.19 |

Figure 9A:
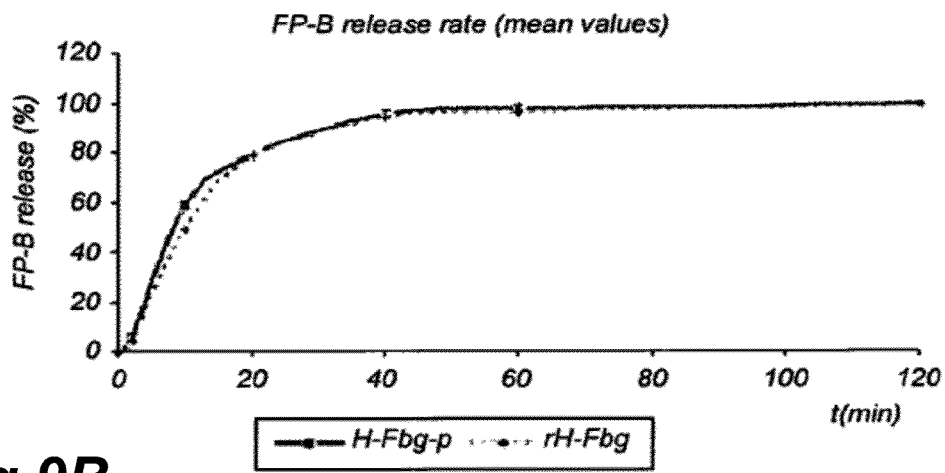
FIGS. 9A, B: The release of fibrinopeptides A, AP and B from plasma-derived fibrinogen (H-Fbg-p) and recombinant Fibrinogen (rh-Fbg) after addition of thrombin. Both fibrinogens (2 mg/ml) were incubated with thrombin (0.095 NIH/ml) and the reaction was stopped at different time points by the addition of 1.1% TFA. Fibrinopeptide AP, -A, -B were separated on a Vydac 218TP52 column as described and for each time point a single analysis was performed. Results are expressed as a % of the maximal release.
Figure 9B:
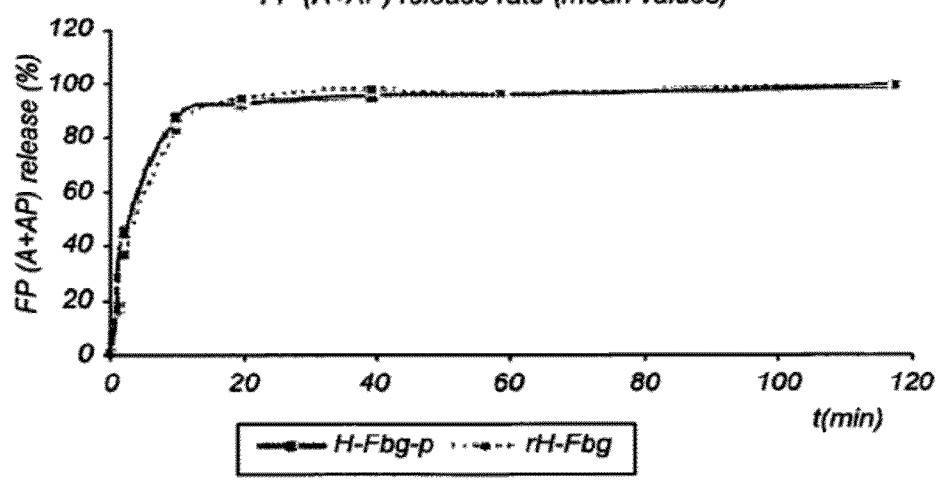

Bands shown in FIG. 9 were analyzed by densitometric analysis and % dimerization was calculated according to the following formula: % Dimerization = γγ-dimer/(γγ-dimer + γ-monomer).

D: Fibrinopeptide Release

Figure 8A:
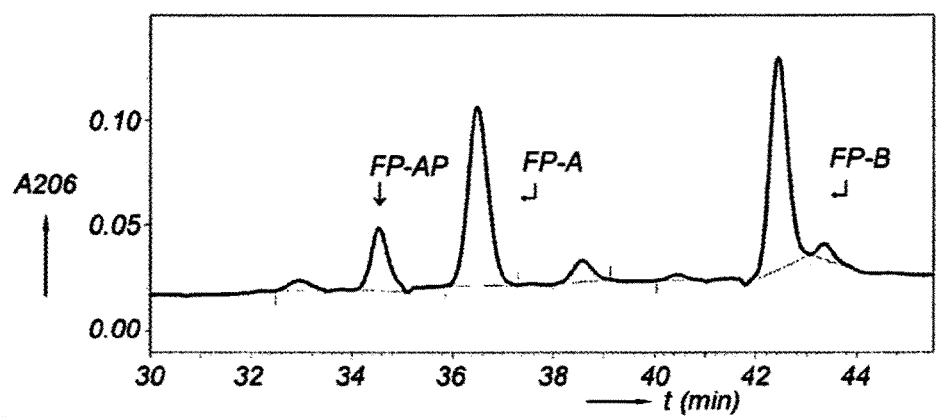
FIGS. 8A, B: Thrombin-catalyzed fibrinopeptides release from plasma-derived (A, upper panel) and recombinant fibrinogen (B lower panel). Both recombinant and plasma-derived fibrinogen (2 mg/ml) were incubated with thrombin (0.91 NIH/ml) for 30 min at 37 ° C. and the reaction was stopped by the addition of 1.1% TFA. Fibrinopeptide AP, -A, -B were separated by HPLC on a Vydac 218TP52 column using a 0.25%/min acetonitrile gradient starting from 10% to 20.5%.
Figure 8B:
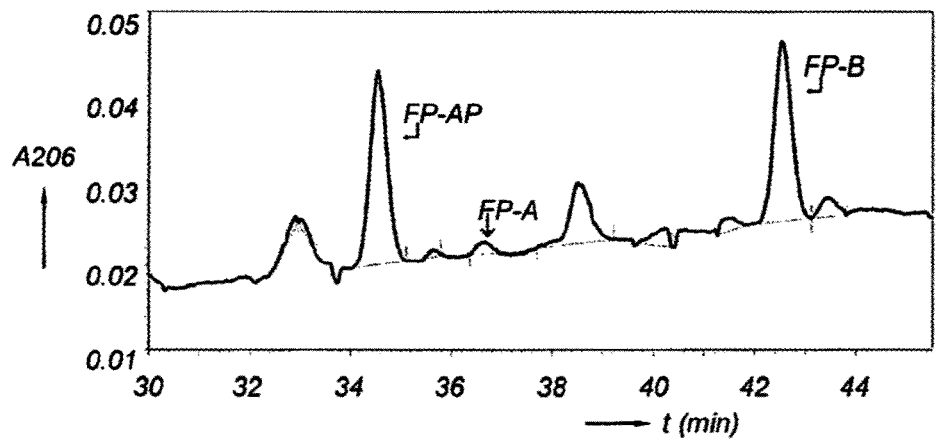

Fibrinopeptides (FP) are released upon binding by thrombin in an ordered manner with FP-A release prior to FP-B release. Blomback, 1978, *Nature* 275: 501. In addition, the serine in FP-A can be phosphorylated which results in the release of FP-AP. When fibrinogen is incubated with a high concentration of thrombin, all fibrinopeptides are released. This total fibrinopeptide release can be analyzed by HPLC analysis. The fibrinopeptide release of both rh-Fbg and h-Fbg were examined and revealed that both fibrinogens display the expected fibrinopeptide profile (FIG. 8). The FP-(A+AP) ratio/FP-B did not differ between the two types of fibrinogen, indicating that the FP-A and FP-B release of the two type of fibrinogens are comparable (Table 4). However, the degree of phosphorylated FP-A was higher in the rh-Fbg preparation (approximately 75% FP-AP) as compared to h-Fbg (~30%).

TABLE 4

Area of the fibrinopeptides released from h-Fbg and rh-Fbg.

| | Area FP-AP | Area FP-A | Area FP-B | Area (A/AP) | Area (A + AP)/B |
|---|---|---|---|---|---|
| h-Fbg | 739806 | 2408847 | 2535823 | 0.31 | 1.24 |
| rh-Fbg | 548998 | 27126 | 589179 | 18.29 | 1.10 |

Rh-Fbg has more FP-AP than FP-A as compared to h-Fbg. The total area of FP-A + FP-AP is about a much as the FP-B area for both types of Fbg's. The % CV of the area is ± 15%.

Next, the rate of thrombin-catalyzed fibrinopeptide release was examined by measuring the peak area's of FP-A, FP-AP and FP-B and plotted against time. As shown in FIG. 9, the release time of FP-A, FP-AP and FP-B for both fibrinogens are highly comparable. For FP-A/AP release the $t_{50}$, i.e. time to reach 50% of the maximal release, for rh-Fbg and h-Fbg is 3.8 and 3.9 minutes respectively. In accordance to literature, Weisel, 1993, *J Mol Biol* 232:285, FP-B release was found to be slower compared to FP-A release and $t_{50}$ was estimated as 10 and 9.3 minutes respectively. These data indicate the rate of fibrinopeptide release is independent of the source of fibrinogen and the degree of phosphorylation.

Example 5

GPRP-Purified Recombinant Fibrinogen

The data reported above were obtained using a recombinant fibrinogen preparation that has been purified by sequential ethanol precipitation. Although this purified fibrinogen was fully functional, the preparation contained a 40 kD impurity. As an alternative purification, recombinant fibrinogen was isolated by affinity purification using the tetrapeptide Gly-Pro-Arg-Pro (GPRP) (SEQ ID NO:1) immobilized to Fractogel. Kuyas, 1990, *Thromb Haemost* 63:439. The Gly-Pro-Arg sequence is involved in the initiation of fibrin polymerization by binding to the complementary binding site of another fibrinogen molecule. Laudano, 1983, *Ann N Y Acad Sci* 408:315. For the isolation of rh-Fbg from cow milk, a defatted milk fraction was loaded onto a GPRP-coupled (SEQ ID NO:1) Toyopearl affinity column Fibrinogen was eluted from the column by lowering the pH. A similar procedure was used for plasma-derived fibrinogen.

Figure 10:
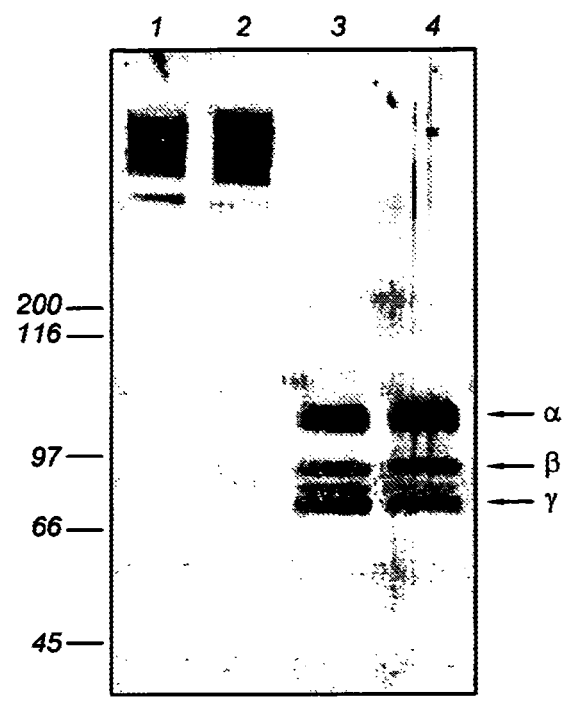
FIG. 10: SDS-PAGE showing recombinant- and plasma-derived fibrinogen. Both recombinant (rh-Fbg) and plasma fibrinogen (h-Fbg) were isolated by GPRP-affinity chromatography and subjected to SDS-PAGE (4-20%) analysis. The proteins were visualized by silver staining. Lane 1 and 2.

By using the GPRP (SEQ ID NO:1) method, both recombinant fibrinogen and human fibrinogen isolated from milk and plasma respectively. The results revealed that the recombinant fibrinogen preparation had a purity of >95% and did not contain the 40 kD impurity (FIG. 10). Similar results were obtained for plasma-derived fibrinogen.

Fibrin polymerization of both GPRP-isolated (SEQ ID NO:1) fibrinogens (rh-Fbg and h-Fbg) was initiated by thrombin and followed in time. As shown in FIG. 11, rh-Fbg has a shorter lag-phase and reaches a higher plateau as compared to h-Fbg. Both preparations show a similar gelation rate. Furthermore, the % clottability of rh-Fbg was 92%, whereas the % clottability of h-Fbg was found to be 98%. These results indicate that rh-Fbg isolated via the GPRP-isolation (SEQ ID NO:1) method is fully functional and highly comparable to h-Fbg.

Cross-linking of the α- and γ-chains was performed in the presence of FXIII and thrombin, and the reaction was analyzed by SDS-PAGE. Both rh-Fbg and h-Fbg showed a similar cross-linking profile (FIG. 12).

Fibrinogen is converted into fibrin by thrombin. This occurs via a fibrinogen recognition site in thrombin, known as exosite 1, Fenton, 1988, *Biochemistry* 27:7106, and results in the cleavage and release of fibrinopeptides A and B. In addition, also fibrin is able to bind thrombin. This interaction is mediated via two non-substrate binding sites, one present in the E-domain, and the other in the D-domain, and results in the inhibition of thrombin. This activity, named antithrombin I, is one of the major mechanisms involved in controlling thrombin activity. A failure of this mechanism may have pathological consequences as indicated by the observation that fibrin from certain congenital dysfibrinogens exhibit reduced thrombin capacity and is associated with severe thromboembolism. Mosesson, 2003, *Thromb Haemost* 89:9.

To determine thrombin binding to fibrin derived from GPRP-isolated (SEQ ID NO:1) rh-Fbg or h-Fbg, both fibrinogens were incubated with thrombin for 30 min at 37° C., the clots were compacted by centrifugation and the residual amount of thrombin activity in the supernatants is determined using the chromogenic S-2238 substrate. As shown in FIG. 13, both recombinant fibrin and h-Fbg are able to bind thrombin. However, the mean % of thrombin binding of rh-Fbg was with 48% less than the thrombin binding capacity of h-Fbg (62%). An explanation for this is not clear.

rh-Fbg, isolated from milk of transgenic cows is structurally and functionally highly comparable to plasma-derived human fibrinogen. Based on SDS-PAGE and western blot analysis, the structures were found to be identical. In addition, both preparations show comparable results in the various functionality tests (summarized in Table 5). Two clear major differences found between rh-fbg and h-Fbg were the amount of FpA phosphorylation, and the glycosylation pattern.

TABLE 5

| | Recombinant Fbg vs Plasma Fbg |
|---|---|
| Polymerization | Comparable |
| Clottability | 92 vs 98% |
| Thrombin binding | 48 vs 62% |
| Platelet aggregation | Comparable |
| FXIII cross-linking | Comparable |
| FpA/B release | Identical |
| FpA phosphorylation | 70 vs 30% |

Example 6

Recombinant Fibrinogen has Reduced Half-Life Relative to Plasma Fibrinogen

The aim of this study was to determine the pharmacokinetics in male Wistar rats of recombinant human Fibrinogen (rhFib) (isolated from cow milk) and plasma derived Fibrinogen (phFib).

Test System
  Test system: Rat: Wistar Wu
  Source: Charles River Laboratories, Sulzfeld, Germany
  Total number of animals: 24 males
  Number/group: 3-5
  Age at start treatment: 10-15 weeks
Test Substance rhFib
  Identification: recombinant human Fibrinogen
  Description: isolated from cow milk by precipitation
  Purity: ~85%
  Composition: 0.5 ml/vial frozen solution in 20 mM NaCitrate pH7.0 and 0.15M NaCl
  Concentration: 15.6 mg/ml (A280)
  Storage: −80° C.
  Stability: Thawed and undiluted: 24 h, 4° C.
Test Substance phFib.
  Identification: plasma derived Fibrinogen
  Description: isolated from human plasma by precipitation
  Batch number: LNB-IV-01-01/36 p36
  Purity: ~90%
  Composition: 0.5 ml/vial frozen solution in 20 mM NaCitrate pH7.0 and 0.15M NaCl
  Concentration: 9.7 mg/ml (A280)
  Storage: −80° C.
  Stability: Thawed and undiluted: 24 h, 4° C.
Test Method
  Method: Intravenous injection into the tail vein or vena cava or vena penis.
  Dose level: See below (under: Allocation)
  Dose volume: ~4 ml/kg
  Dosing speed: ~1 ml/10 sec
Allocation of Test Groups

TABLE 6

| Group | Test substance | Compound or Batch | Dose level mg/kg | Number of animals | Animal numbers | | |
|---|---|---|---|---|---|---|---|
| 1 | PBS | N.A. | N.A. | 3 | 53.2 | 54.1 | 54.2 |
| 2 | rhFib | Prec. Cow milk #204 | 4 | 3 | 52.1 | 52.2 | 53.1 |
| 3 | phFib | Prec. human plasma | 4 | 3 | 55.1 | 55.2 | 56.1 |

Treatment of Test and Control Animals
  Rats were anaesthetized by subcutaneous injection of 2.7 ml/kg of hypnorm/midazolam (end concentration: fentanylcitrate: 0.08 mg/ml; fluanison: 2.5 mg/ml; midazolam 1.25 mg/ml) and the abdomen was opened.
  The test items were injected via the tail vein or vena cava or vena penis. At the indicated times, blood samples of approximately 0.2 ml were taken from the inferior vena cava and transferred to eppendorff vials with 10 ml of 0.5 M EDTA in PBS.
  The samples were centrifuged for 5 min at 3500×g and 100 ml plasma of each sample is stored at −20° C. upon analysis.
Blood Sampling
  Blood samples were taken on each of the following time points:
    −5 (pre-dose), 2, 5, 10, 15, 20, 30, 45 and 60 minutes after end of Fib dosing
Assay
  The concentration of human Fib in the plasma samples was determined using an ELISA for the detection of rhFib.

| PHARMACOKINETIC EVALUATION | | |
|---|---|---|
| 1. | ERC | Elimination Rate Constant |
| 2. | T½ | Half-life |
| 3. | AUC 0-t | Area under the curve, from 0 till the last quantifiable point |
| 4. | AUC 0-inf | Area under the curve, from 0 till infinity |

Plasma Clearance Results

TABLE 7

Overview of tested substances, body weight

| | Test Substance | Batch | inj dose mg/kg | Rat no | weight g |
|---|---|---|---|---|---|
| Group 1 | PBS | N.A. | N.A. | 53.2 | 213 |
| | | | N.A. | 54.1 | 210 |
| | | | N.A. | 54.2 | 218 |
| Group 2 | rhFib | Prec. from cowmilk #204 | 4 | 52.1 | 218 |
| | | | 4 | 52.2 | 209 |
| | | | 4 | 53.1 | 211 |
| Group 3 | phFib | Prec. From human plasma | 4 | 55.1 | 265 |
| | | | 4 | 55.2 | 299 |
| | | | 4 | 56.1 | 275 |

TABLE 8

Overview of recording of data of analysis

| | Test Substance | Batch | inj dose U/kg | Rat no |
|---|---|---|---|---|
| Group 1 | PBS | N.A. | N.A. | 53.2 |
| | | | N.A. | 54.1 |
| | | | N.A. | 54.2 |

TABLE 8-continued

Overview of recording of data of analysis

| Test Substance | Batch | inj dose U/kg | Rat no |
|---|---|---|---|
| Group 2 rhFib | Prec. from cowmilk #204 | 4 | 52.1 |
| | | 4 | 52.2 |
| | | 4 | 53.1 |
| Group 3 phFib | Pcec. From human plasma | 4 | 55.1 |
| | | 4 | 55.2 |
| | | 4 | 56.1 |

Clearance Data

TABLE 9

Clearance data of rh-Fibrinogen

| | Rat 1 | Rat 2 | Rat 3 | | |
|---|---|---|---|---|---|
| Rat No | 52.1 | 52.2 | 53.1 | | |
| Weight | 218 | 209 | 211 | | |
| Time (min) | ug/ml | ug/ml | ug/ml | Mean | st dev |
| 0 | | | | | |
| 2 | 47 | 30 | 32 | 36 | 9 |
| 5 | 42 | 32 | 34 | 36 | 5 |
| 10 | 34 | 33 | 28 | 32 | 3 |
| 15 | 30 | 30 | 25 | 28 | 3 |
| 20 | 26 | 19 | 17 | 21 | 5 |
| 30 | 24 | 7 | 12 | 14 | 9 |
| 45 | 19 | 12 | 11 | 14 | 4 |
| 60 | 17 | 15 | 9 | 14 | 4 |

TABLE 10

Clearance data of ph-Fibrinogen

| | Rat 1 | Rat 2 | Rat 3 | | |
|---|---|---|---|---|---|
| Rat No | 55.1 | 55.2 | 56.1 | | |
| Weight | 265 | 299 | 275 | | |
| Time (min) | ug/ml | ug/ml | ug/ml | Mean | st dev |
| 0 | | | | | |
| 2 | 143 | 128 | 104 | 125 | 20 |
| 5 | 131 | 125 | 104 | 120 | 14 |
| 10 | 163 | 128 | 106 | 132 | 29 |
| 15 | 162 | 55 | 118 | 112 | 54 |
| 20 | 141 | 41 | 94 | 92 | 50 |
| 30 | 132 | 83 | 90 | 102 | 27 |
| 45 | 133 | 83 | 97 | 104 | 26 |
| 60 | 138 | 83 | 87 | 103 | 31 |

Pharmacokinetic Results

TABLE 11

Pharmacokinetic data of rh-Fibrinogen

| Rat No | Rat 1 52.1 | Rat 2 52.2 | Rat 3 53.1 | Mean | st dev |
|---|---|---|---|---|---|
| ERC | 0.017 | 0.019 | 0.024 | 0.020 | 0.004 |
| T½ | 41 | 36 | 28 | 35 | 6 |
| AUC0-t | 1466 | 1011 | 959 | 1145 | 279 |
| AUC0-inf | 2472 | 1793 | 1327 | 1864 | 576 |

TABLE 12

Pharmacokinetic data of ph-Fibrinogen

| | Rat 1 | Rat 2 | Rat 3 | | |
|---|---|---|---|---|---|
| Rat No | 55.1 | 55.2 | 56.1 | Mean | st dev |
| ERC | 0.002 | 0.006 | 0.003 | 0.004 | 0.002 |
| T½ | 444 | 120 | 202 | 255 | 168 |
| AUC0-t | 8101 | 4820 | 5630 | 6183 | 1709 |
| AUC0-inf | 96507 | 19228 | 30997 | 48911 | 41638 |

TABLE 13

Pharmacokinetical parameter overview

| | Group 1 Control | | Group 2 rh-Fibrinogen | | Group 3 Plasma Fibrinogen | |
|---|---|---|---|---|---|---|
| Parameter | Mean | STD | Mean | STD | Mean | STD |
| ERC | N.D. | | 0.020 ± 0.004 | | 0.004 ± 0.002 | |
| T½ | N.D. | | 35 ± 6 | | 255 ± 168 | |
| AUC$_{0-t}$ | N.D. | | 1145 ± 279 | | 6183 ± 1709 | |
| AUC$_{0-\infty}$ | N.D. | | 1864 ± 576 | | 48911 ± 41638 | |

TABLE 14

T-test on half-life and AUC0-inf data

| | Half-life | | AUC0-inf | |
|---|---|---|---|---|
| | rH-Fbg | pH-Fbg | rH-Fbg | pH-Fbg |
| Mean | 35 | 255 | 1864 | 48911 |
| Variance | 41 | 28336 | 331854 | 1733703590 |
| Observations | 3 | 3 | 3 | 3 |
| Pooled Variance | 14189 | | 9E+08 | |
| Hypothesized Mean Difference | 0 | | 0 | |
| Df | 4 | | 4 | |
| t Stat | −2.27 | | −1.96 | |
| P(T <= t) one-tail | 0.04 | | 0.06 | |
| t Critical one-tail | 2.13 | | 2.13 | |
| P(T <= t) two-tail | 0.09 | | 0.12 | |
| t Critical two-tail | 2.78 | | 2.78 | |

Figure 14B:
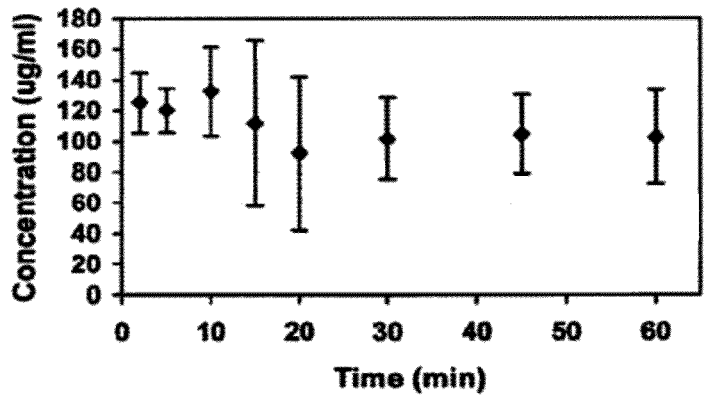

The data are summarized in FIG. 14. There is a significant difference in the half-life of rh-Fibrinogen compared to plasma fibrinogen. All publications, patents and patent applications cited are herein incorporated by reference in their entirety for all purposes to the same extent as if each individual publication, patent and patent application was specifically and individually indicated to be incorporated by reference in its entirety for all purposes. Unless otherwise apparent from the context, any step, element, embodiment, feature or aspect of the present application can be combined with any other step, element, embodiment, feature or aspect.

The invention claimed is:

1. A method of treating or effecting prophylaxis in a patient who is bleeding or is at risk of bleeding, comprising administering a dose of recombinant fibrinogen having a reduced half-life relative to natural human plasma fibrinogen to the patient, wherein the peak plasma concentration of recombinant fibrinogen is greater than 1 g/L.

2. The method according to claim 1, wherein the recombinant fibrinogen is under-sialyated.

3. The method according to claim 1, wherein the recombinant fibrinogen is recombinant human fibrinogen.

4. The method according to claim 1, wherein the half-life of the recombinant fibrinogen is reduced by a factor of at least 50% relative to that of human plasma fibrinogen.

5. The method according to claim 1, wherein the dose is greater than 1 g.

6. The method according to claim 1, wherein the dose delivers a peak plasma concentration of recombinant and endogenous fibrinogen greater than 2 g/L.

7. The method according to claim 1, wherein the bleeding results from an acute disorder, a traumatic injury, surgery, or an inherited disorder.

8. A method of treating or effecting prophylaxis in a patient who is bleeding or at risk of bleeding, comprising administering fibrinogen having a reduced half-life relative to natural human plasma fibrinogen to the patient, wherein the treatment is in a regime sufficient to achieve a peak concentration of fibrinogen in plasma including administered and endogenous fibrinogen that is within or above normal levels, and wherein the plasma concentration declines to normal or below normal levels within three days of first administration.

9. The method according to claim 8, wherein the peak plasma concentration of fibrinogen including administered and endogenous fibrinogen is above 2 g/L.

10. The method according to claim 8, wherein the peak plasma concentration of fibrinogen including administered and endogenous fibrinogen is within 2-4 g/L and the plasma concentration of fibrinogen declines below 2 g/L within one day.

11. The method according to claim 8, wherein the regime is such that fibrinogen is administered once or at multiple times occurring within a period of no more than two hours.

12. The method according to claim 8, wherein the regime is such that fibrinogen is administered multiple times at intervals no greater than two days.

13. The method of claim 4, wherein the half life of the recombinant fibrinogen is less than one day.

14. The method of claim 7, wherein the bleeding results from an inherited deficiency in a coagulation protein.

* * * * *

UNITED STATES PATENT AND TRADEMARK OFFICE
CERTIFICATE OF CORRECTION

PATENT NO. : 8,557,773 B2  
APPLICATION NO. : 12/990643  
DATED : October 15, 2013  
INVENTOR(S) : Pieper et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 200 days.

Signed and Sealed this  
Seventh Day of April, 2015

Michelle K. Lee  
*Director of the United States Patent and Trademark Office*